US012735468B2

(12) United States Patent
Sayós Ortega et al.

(10) Patent No.: US 12,735,468 B2
(45) Date of Patent: Sep. 15, 2026

(54) CELL-PENETRATING PEPTIDES

(71) Applicant: FUNDACIÓ HOSPITAL UNIVERSITARI VALL D'HEBRON—INSTITUT DE RECERCA, Barcelona (ES)

(72) Inventors: Juan Sayós Ortega, Barcelona (ES); Simón Schwartz Navarro, Sabadell (ES); Joaquin Seras Franzoso, Mataró (ES); Águeda Martínez Barriocanal, Barcelona (ES); Diana Fernandes De Sousa Rafael, Barcelona (ES); Fernanda Raquel Da Silva Andrade, Barcelona (ES)

(73) Assignee: FUNDACIO HOSPITAL UNIVERSITARI VALL D'HEBRON-INSTITUT DE RECERCA, Barcelona (ES)

( * ) Notice: Subject to any disclaimer, the term of this patent is extended or adjusted under 35 U.S.C. 154(b) by 669 days.

(21) Appl. No.: 18/036,329

(22) PCT Filed: Nov. 9, 2021

(86) PCT No.: PCT/EP2021/081100
§ 371 (c)(1),
(2) Date: May 10, 2023

(87) PCT Pub. No.: WO2022/101193
PCT Pub. Date: May 19, 2022

(65) Prior Publication Data

US 2023/0416334 A1 Dec. 28, 2023

(30) Foreign Application Priority Data

Nov. 10, 2020 (EP) .................................... 20382968

(51) Int. Cl.

*C07K 14/00* (2006.01)
*A61K 47/62* (2017.01)
*A61K 47/69* (2017.01)
*C07K 14/705* (2006.01)

(52) U.S. Cl.

CPC ........ *C07K 14/70503* (2013.01); *A61K 47/62* (2017.08); *A61K 47/6901* (2017.08); *A61K 47/6907* (2017.08)

(58) Field of Classification Search

CPC .............. C07K 14/70503; A61K 47/62; A61K 47/6901; A61K 47/6907; A61K 47/6455; A61K 38/00; C12N 15/88
See application file for complete search history.

(56) References Cited

U.S. PATENT DOCUMENTS

| | | | | |
|---|---|---|---|---|
| 2005/0226812 | A1* | 10/2005 | Emtage | G01N 33/57426 424/1.49 |
| 2010/0291108 | A1 | 11/2010 | Abo et al. | |
| 2018/0252712 | A1* | 9/2018 | Virgin | G01N 33/56983 |

FOREIGN PATENT DOCUMENTS

| | | | |
|---|---|---|---|
| CA | 3040645 | A1 | 10/2020 |
| WO | WO 01/00673 | A1 | 1/2001 |
| WO | WO 2008/050830 | A1 | 5/2008 |
| WO | WO2014001509 | A1 | 1/2014 |
| WO | WO 2019/129657 | A1 | 7/2019 |
| WO | WO 2020/014097 | A1 | 1/2020 |
| WO | WO 2020/152298 | A1 | 7/2020 |

OTHER PUBLICATIONS

Kristensen et al. Int. J. Mol. Sci. 2016, 17, 185; doi:10.3390/ijms 17020185.*
Sino Biological, https://www.sinobiological.com/resource/cd300f-cd300lf, 2007-2025, last visited Nov. 29, 2025.*
National Institute of Cancer—understanding and related topics, accessed Nov. 29, 2025 at URL: https://www.cancer.gov/about-cancer/understanding/what-is-cancer.*
International Search Report and Written Opinion mailed Feb. 23, 2022 for Application No. PCT/EP2021/081100; 15 pages.
Altschul et al., "Basic local alignment search tool", J. Mol. Biol 1990; vol. 215, pp. 403-410.
Andrade, F., et al., "Biological assessment of self-assembled polymeric micelles for pulmonary administration of insulin", (Accepted Manuscript) Nanomedicine 2015; vol. 11(7), pp. 1621-1631.
Chichili, et al., "Linkers in the structural biology of protein-protein interactions", Protein Sci. 2013 (published online Dec. 6, 2012); vol. 22(1); pp. 153-167.
Copolovici, et al., "Cell-Penetrating Peptides: Design, Synthesis, and Applications", ACS Nano; Feb. 24, 2014, vol. 8 (3), pp. 1972-1994.

(Continued)

*Primary Examiner* — Jeanette M Lieb
(74) *Attorney, Agent, or Firm* — Squire Patton Boggs (US) LLP

(57) ABSTRACT

The present invention provides a peptide of a length from 10 to 50 amino acid residues, which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid, in particular, which comprises the amino acid sequence $LKXaa_1WXaa_2Xaa_3GAIW$ (SEQ ID NO: 19), wherein $Xaa_1$, $Xaa_2$, and $Xaa_3$, are each independently any amino acid. The invention also provides a conjugate comprising the peptide, a pharmaceutical composition comprising the conjugate, a method for delivering a cargo into a cell, a nucleic acid molecule encoding the peptide, and a host cell comprising said nucleic acid molecule.

9 Claims, 5 Drawing Sheets

Specification includes a Sequence Listing.

(56) References Cited

OTHER PUBLICATIONS

Izawa, et al., "Sphingomyelin and ceramide are physiological ligands for human LMIR/ CD 300f, inhibiting FCepsilonRI-mediated mast cell activation", Journal of Allergy and Clinical Immunology; Jan. 1, 2014; vol. 133(1); p. 270.
Lee, et al., "Synthetic peptides containing ITIM-like sequences of IREM-1 CD300F) differentially regulate MyD88 and TRIF-mediated TLR signalling through activation of SHP and/or PI3K", Clinical and Experimental Immunology; Jan. 30, 2012; vol. 167(3); pp. 438-446.

* cited by examiner

CELL-PENETRATING PEPTIDES

CROSS-REFERENCE TO RELATED APPLICATION(S)

The present application is a National Stage filing under 35 U.S.C. $371 of International Patent Application No. PCT/EP2021/081100, filed Nov. 10, 2020, which claims the benefit of the European Patent Application No. 20382968.4 filed Nov. 10, 2020, the contents of all of which are hereby incorporated by reference in their entireties for all purposes.

TECHNICAL FIELD

The present invention relates to the field of intracellular delivery of molecules, more particularly, to cell-penetrating peptides. The invention also relates to conjugates comprising a cell-penetrating peptide and a cargo.

BACKGROUND ART

The cell plasma membrane represents an efficient barrier that prevents most molecules from cellular uptake, which also hampers the targeted delivery of molecules, such as therapeutic substances.

Only a small range of molecules having a particular molecular weight, polarity and/or net charge are able to passively diffuse through cell membranes. All other molecules have to be actively transported, e.g., by receptor-mediated endocytosis or via ATP-binding transporter molecules.

Several strategies have been developed to deliver molecules by artificially forcing them to pass the cell membrane, for example by means of electroporation, micro-injection, and viral delivery. However, these methods have various drawbacks, including low efficiency, high toxicity, poor bioavailability, and low specificity, which have prevented them from becoming an efficient tool for the delivery of drugs or other therapeutically active agents to cells.

One of the most promising alternatives for delivering cargos into cells are cell-penetrating peptides (CPPs), which are peptides that are able to cross cell membranes and facilitate the cellular uptake of the molecular cargo they are attached to. Despite several decades of investigation, the fundamental basis for CPPs activity remains elusive. Consequently, CPPs developed so far do not usually achieve a high efficiency in cargo delivery and are frequently cytotoxic for cells.

Therefore, in spite of the efforts made so far, there is still a need for improved CPPs with high delivery efficiency and low toxicity.

SUMMARY OF INVENTION

The present inventors have developed various CPPs to deliver cargos inside cells with very high efficiency and without noticeable toxicity.

The inventors found that peptides comprising a specific short amino acid sequence of the CD300f protein show a strong binding capacity to phospholipids, the main component of the plasma membrane (see FIGS. 1 and 2 below). Through amino acid substitutions, the inventors found the key amino acids that mediate the binding of this sequence being, in particular, one lysine residue located in the second position and two tryptophan residues located in the fourth and tenth positions.

Surprisingly, the inventors found that peptides or proteins comprising the identified sequence show a potent cell-penetration activity, thereby facilitating the internalization of cargos to which they are conjugated (see FIGS. 3, 4, 5 and 6 below).

Notably, as shown in the examples below, micelles conjugated to the peptides of the invention present higher delivery rates than micelles conjugated to TAT, the gold standard of CPPs.

All these characteristics make the peptides of the invention an important molecular tool for the delivery of substances to cells.

Thus, in a first aspect, the invention provides a peptide of a length from 10 to 50 amino acid residues, which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid, in particular, which comprises the amino acid sequence $LKXaa_1WXaa_2Xaa_3GAIW$ (SEQ ID NO: 19), wherein $Xaa_1$, $Xaa_2$, and $Xaa_3$, are each independently any amino acid.

In a second aspect, the invention provides a conjugate comprising a peptide or a protein, which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid; in particular, comprising a peptide as defined in the first aspect; and a cargo.

The inventors found that the CPP activity of the identified sequences was maintained even when the sequence was part of long amino acid chains, such as the whole CD300f protein, which naturally contains the sequence of the invention (see FIG. 5).

In a particular embodiment of the second aspect of the invention, optionally in combination with any of the embodiments provided above or below, the peptide is of a length from 10 to 50 amino acid residues, and the protein is of a length from 51 to 400 amino acid residues.

In a third aspect, the invention provides a pharmaceutical composition comprising a therapeutically effective amount of a conjugate as defined in the second aspect with at least one pharmaceutically acceptable excipient, diluent or carrier.

In a fourth aspect, the invention provides a conjugate as defined in the second aspect or a pharmaceutical composition as defined in the third aspect for use as a medicament, in particular wherein the cargo comprises a therapeutic agent. Also, the invention provides a conjugate as defined in the second aspect or a pharmaceutical composition as defined in the third aspect for use in therapy, in particular wherein the cargo comprises a therapeutic agent.

In a fifth aspect, the invention provides a conjugate as defined in the second aspect or a pharmaceutical composition as defined in the third aspect for use in in vivo diagnosis and/or prognosis, in particular wherein the cargo comprises a labelling agent.

In a sixth aspect, the invention provides an in vitro method for delivering a cargo into a cell, the method comprising administering the conjugate as defined in the second aspect or the pharmaceutical composition as defined in the third aspect to a cell.

In a seventh aspect, the invention provides a polynucleotide, which encodes the peptide as defined in the first aspect.

In an eighth aspect, the invention provides a vector comprising the polynucleotide as defined in the seventh aspect.

In a ninth aspect, the invention provides a host cell which is transformed or transfected with the polynucleotide as defined in the seventh aspect or the vector as defined in the eighth aspect.

In a tenth aspect, the invention provides a cell culture comprising the host cell as defined in the ninth aspect.

In an eleventh aspect, the invention provides a process for the production of a peptide as defined in the first aspect, comprising: (a) culturing the host cell as defined in the ninth aspect under suitable conditions, or, alternatively, (b) in vitro transcription and/or translation of the polynucleotide as defined in the first aspect; and (c) isolating the resulting peptide.

In a twelfth aspect, the invention provides a process for the production of a conjugate as defined in the second aspect, comprising the steps (a) providing a peptide or protein which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4Xaa_5$, $Xaa_6$ and $Xaa_7$ are each independently any amino acid, in particular, the amino acid sequence $LKXaa_1WXaa_2Xaa_3GAIW$ (SEQ ID NO: 2), wherein $Xaa_1$, $Xaa_2$, and $Xaa_3$, are each independently any amino acid, more in particular the peptide of the first aspect; and (b) conjugating the at least one peptide or protein of (a) with a cargo.

In a thirteenth aspect, the invention provides a kit of parts comprising (a) a peptide as defined in the first aspect; (b) optionally, a cargo; and (c) optionally, instructions for its use.

In a fourteenth aspect, the invention provides the use of a peptide or protein which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid, in particular, the amino acid sequence $LKXaa_1WXaa_2Xaa_3GAIW$ (SEQ ID NO: 19), wherein $Xaa_1$, $Xaa_2$, and $Xaa_3$, are each independently any amino acid, as a cell-penetrating peptide for transporting a cargo inside a cell in vitro, wherein the peptide or protein is conjugated to the cargo.

In a fifteenth aspect, the invention provides a process for the production of a conjugate comprising a peptide as defined in the first aspect and a extracellular vesicle (EV) cargo, the process comprising (a) culturing the host cell as defined in the ninth aspect under suitable conditions, and (b) isolating the resulting conjugate formed by the peptide conjugated to the extracellular vesicle of the host cell.

DETAILED DESCRIPTION OF THE INVENTION

Figure 1:
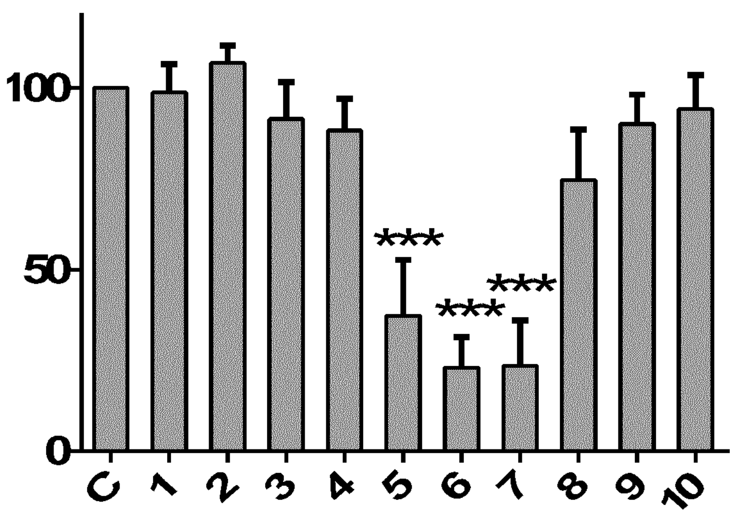
FIG. 1, related to Example 1, is a bar diagram showing the binding capacity of the indicated peptides to sphingomyelin (SM). They y-axis represents absorbance (%). "C" represents the control; "1" represents Peptide 1 of SEQ ID NO: 12; "2" represents Peptide 2 of SEQ ID NO: 13; "3" represents Peptide 3 of SEQ ID NO: 14; "4" represents Peptide 4 of SEQ ID NO: 15; "5" represents Peptide 5 of SEQ ID NO: 5; "6" represents Peptide 6 of SEQ ID NO: 6; "7" represents Peptide 7 of SEQ ID NO: 7; "8" represents Peptide 8 of SEQ ID NO: 16; and "9" represents Peptide 9 of SEQ ID NO: 17; and "10" represents Peptide 10 of SEQ ID NO: 18.
Figure 1:
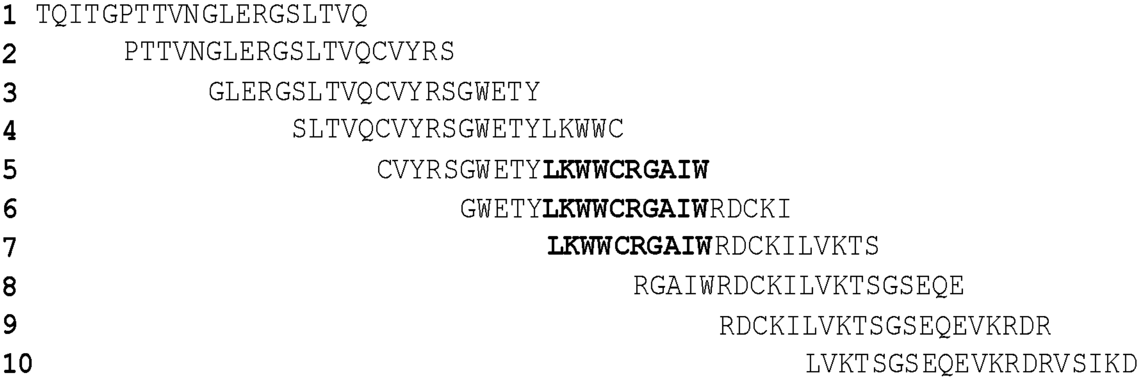

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

For the purposes of the invention, any ranges given include both the lower and the upper end-points of the range.

As above disclosed, the present inventors have developed a set of peptides with a high capacity to act as cell-penetration peptides.

In the present invention, the term "amino acid" refers to a molecule containing both an amino group and a carboxyl group. Amino acids can be classified by the side chain group. There are basically four different classes of amino acids determined by different side chains: (1) non-polar, (2) polar and neutral, (3) acidic and polar, (4) basic and polar.

Non-polar amino acids have side chains, which are hydrocarbon alkyl groups (alkane branches) or aromatic (benzene rings) or heteroaromatic (e.g. indole ring). Illustrative non-limitative examples of common non-polar amino acids are Ala, Val, Leu, Ile, Pro, Trp, Gly, Phe, and Met.

Polar-neutral amino acids have polar but not charged groups at neutral pH in the side chain (such as hydroxyl, amide or thiol groups). Illustrative non-limitative examples of polar neutral amino acids are Ser, Thr, Cys, Tyr, Asn, and Gln.

Acid amino acids (hereinafter also referred as "acid and polar amino acid") have acidic side chains at neutral pH. These are aspartic acid or aspartate (Asp) and glutamic acid or glutamate (Glu), among others. Their side chains have carboxylic acid groups whose pKa's are low enough to lose protons, becoming negatively charged in the process.

Basic amino acids (hereinafter also referred as "basic and polar amino acid") have side chains containing nitrogen and resemble ammonia, which is a base (such as amines, guanidines, or imidazole). Their pKa's are high enough that they tend to bind protons, gaining a positive charge in the process. Illustrative non-limitative examples of basic amino acids are Lys, Arg, and His.

Suitable amino acids include, without limitation, alpha amino acids, such as the L-isomers of alpha-amino acids of the 20 common naturally occurring alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; natural beta-amino acids (e.g., beta-alanine); and unnatural amino acids.

The term "unnatural amino acid" comprises D-isomers of the 20 common naturally occurring alpha-amino acids or amino acids of formula (A)

(A)

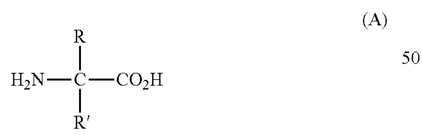

wherein R and R' have the meaning provided in Table 1 below. Further illustrative non-limitative examples of unnatural amino acids are summarized in Table 2:

TABLE 1

| Exemplary unnatural alpha-amino acids | Suitable amino acid side chains R | R' |
|---|---|---|
| D-Alanine | —H | $—CH_3$ |
| D-Arginine | —H | $—CH_2CH_2CH_2—NHC(=NH)NH_2$ |
| D-Asparagine | —H | $—CH_2C(=O)NH_2$ |
| D-Aspartic acid | —H | $—CH_2CO_2H$ |
| D-Cysteine | —H | $—CH_2SH$ |
| D-Glutamic acid | —H | $—CH_2CH_2CO_2H$ |
| D-Glutamine | —H | $—CH_2CH_2C(=O)NH_2$ |
| D-Histidine | —H | $—CH_2$-2-(1H-imidazole) |
| D-Isoleucine | —H | -sec-butyl |
| D-Leucine | —H | -iso-butyl |
| D-Lysine | —H | $—CH_2CH_2CH_2CH_2NH_2$ |
| D-Methionine | —H | $—CH_2CH_2SCH_3$ |
| D-Phenylalanine | —H | $—CH_2Ph$ |
| D-Proline | —H | -2-(pyrrolidine) |
| D-Serine | —H | $—CH_2OH$ |
| D-Threonine | —H | $—CH_2CH(OH)(CH_3)$ |
| D-Tryptophan | —H | $—CH_2$-3-(1H-indole) |
| D-Tyrosine | —H | $—CH_2$-(p-hydroxyphenyl) |
| D-Valine | —H | -isopropyl |
| Di-vinyl | $—CH=CH_2$ | $—CH=CH_2$ |
| **Exemplary unnatural alpha-amino acids** | **R and R' are equal to:** | |
| α-methyl-Alanine (Aib) | $—CH_3$ | $—CH_3$ |
| α-methyl-Arginine | $—CH_3$ | $—CH_2CH_2CH_2—NHC(=NH)NH_2$ |
| α-methyl-Asparagine | $—CH_3$ | $—CH_2C(=O)NH_2$ |
| α-methyl-Aspartic acid | $—CH_3$ | $—CH_2CO_2H$ |
| α-methyl-Cysteine | $—CH_3$ | $—CH_2SH$ |
| α-methyl-Glutamic acid | $—CH_3$ | $—CH_2CH_2CO_2H$ |
| α-methyl-Glutamine | $—CH_3$ | $—CH_2CH_2C(=O)NH_2$ |
| α-methyl-Histidine | $—CH_3$ | $—CH_2$-2-(1H-imidazole) |
| α-methyl-Isoleucine | $—CH_3$ | -sec-butyl |
| α-methyl-Leucine | $—CH_3$ | -iso-butyl |
| α-methyl-Lysine | $—CH_3$ | $—CH_2CH_2CH_2CH_2NH_2$ |

TABLE 2

| | |
|---|---|
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4 Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| alle | allo-Isoleucine |
| Nva | Norvaline |
| Nle | Norleucine |
| Orn | Ornithine |

Each one of the amino acids forming the peptide of the invention can have, independently from the others, L- or D-configuration. In one embodiment of the first aspect of the invention, optionally in combination with any one of the embodiments provided below, the amino acid residue at the amine-terminal end N(t) and/or the amino acid residue at the carboxyl-terminal end C(t) has D-configuration.

Amino acids used in the preparation of the peptides of the present invention may be prepared by organic synthesis, or obtained by other routes, such as, for example, degradation of or isolation from a natural source.

As used herein, the term "peptide" is used interchangeably with the term "polypeptide" and refers to chains from 2 to 50 amino acid residues. The term "protein" refers to chains of more than 50 amino acid residues.

In one embodiment of the first aspect of the invention, optionally in combination with any one of the embodiments provided below, the peptide is a cell-penetrating peptide.

As used herein, a "cell-penetrating peptide" or "CPP" refers to peptides or proteins that are able to transport across the plasma a cargo to which they are conjugated, thereby facilitating the cellular uptake of the cargo. Depending on the particular case, the cargo molecule can, then, be released in the cytoplasm, directed to an intracellular organelle, or further presented at the cell surface. Cell penetrating ability, or internalization, of the cell-penetrating peptide or conjugate comprising said cell-penetrating peptide can be checked by standard methods known to one skilled in the art, including flow cytometry or fluorescence microscopy of live and fixed cells, immunocytochemistry of cells transduced with said peptide or conjugate, and Western blot.

In an embodiment of the first aspect of the invention, optionally in combination with any one of the embodiments provided below, the peptide comprises the amino acid sequence $Xaa_1KXaa_2WXaa_3Xaa_4Xaa_5Xaa_6Xaa_7W$ (SEQ ID NO: 1), wherein at least one of $Xaa_1$ to $Xaa_7$ is selected from the group consisting of: $Xaa_1$, $Xaa_2$, $Xaa_5$, $Xaa_6$ and $Xaa_7$ are each independently a non-polar amino acid; and $Xaa_3$ and $Xaa_4$ are each independently a polar amino acid.

In an embodiment of the first aspect of the invention, optionally in combination with any one of the embodiments provided below, the peptide comprises the amino acid sequence $Xaa_1KXaa_2WXaa_3Xaa_4Xaa_5Xaa_6Xaa_7W$ (SEQ ID NO: 1), wherein at least one of $Xaa_1$ to $Xaa_7$ is selected from the group consisting of: $Xaa_1$, $Xaa_2$, $Xaa_5$, $Xaa_6$ and $Xaa_7$ are each independently a non-polar amino acid; $Xaa_3$ is a polar-neutral amino acid; and $Xaa_4$ is a basic amino acid. This embodiment can also be formulated as the peptide comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$, $Xaa_5$, $Xaa_6$ and $Xaa_7$ are each independently a non-polar amino acid; $Xaa_3$ is a polar-neutral amino acid; and/or $Xaa_4$ is a basic amino acid.

In a particular embodiment of the first aspect of the invention, optionally in combination with any one of the embodiments provided below, the peptide comprises the amino acid sequence $Xaa_1KXaa_2WXaa_3Xaa_4Xaa_5Xaa_6Xaa_7W$ (SEQ ID NO: 1), wherein at least one of $Xaa_1$ to $Xaa_7$ is selected from the group consisting of: $Xaa_1$ is selected from leucine and isoleucine; $Xaa_2$ is selected from tryptophan and alanine; $Xaa_3$ is selected from cysteine and serine; $Xaa_4$ is selected from arginine and glycine; $Xaa_5$ is selected from glycine and alanine; $Xaa_6$ is selected from glycine and alanine; and $Xaa_7$ is selected from leucine and isoleucine. This is meant to include all the combinations where only one, only two, only three, only four, only five, only six, or all seven amino acids have the particular identities indicated.

In an embodiment of the first aspect of the invention, optionally in combination with any one of the embodiments provided below, the peptide comprises the amino acid sequence $LKXaa_1WXaa_2Xaa_3GAIW$ (SEQ ID NO: 19), wherein at least one of $Xaa_1$ to $Xaa_3$ is selected from the group consisting of: $Xaa_1$ is a non-polar amino acid; and $Xaa_2$ and $Xaa_3$ are each independently a polar amino acid. In another particular embodiment, the peptide comprises the amino acid sequence $LKXaa_1WXaa_2Xaa_3GAIW$ (SEQ ID NO: 19), wherein at least one of $Xaa_1$ to $Xaa_3$ is selected from the group consisting of: $Xaa_1$ is a non-polar amino acid; $Xaa_2$ is a polar-neutral amino acid; and $Xaa_3$ is a basic amino acid. In a more particular embodiment, the peptide comprises the amino acid sequence $LKXaa_1WXaa_2Xaa_3GAIW$ (SEQ ID NO: 19), wherein at least one of $Xaa_1$ to $Xaa_3$ is selected from the group consisting of: $Xaa_1$ is selected from tryptophan and alanine; $Xaa_2$ is selected from cysteine and serine; and $Xaa_3$ is selected from arginine and glycine.

In one embodiment of the first aspect of the invention, optionally in combination with any one of the embodiments provided below, the peptide comprises the amino acid sequence LKWWCRGAIW (SEQ ID NO: 2), or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 2. In a more particular embodiment, the peptide consists of the amino acid sequence LKWWCRGAIW (SEQ ID NO: 2) or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 2.

In one embodiment of the first aspect of the invention, optionally in combination with any one of the embodiments provided below, the peptide comprises the amino acid sequence $LKXaa_1W\ Xaa_2Xaa_3GAIWRDCK$ (SEQ ID NO: 20) wherein at least one of $Xaa_1$ to $Xaa_3$ is selected from the group consisting of: $Xaa_1$ is a non-polar amino acid; and $Xaa_2$ and $Xaa_3$ are each independently a polar amino acid. In another particular embodiment, the peptide comprises the amino acid sequence $LKXaa_1W\ Xaa_2Xaa_3GAIWRDCK$ (SEQ ID NO: 20), wherein at least one of $Xaa_1$ to $Xaa_3$ is selected from the group consisting of: $Xaa_1$ is a non-polar amino acid; $Xaa_2$ is a polar-neutral amino acid; and $Xaa_3$ is a basic amino acid. In a more particular embodiment, the peptide comprises the amino acid sequence $LKXaa_1W\ Xaa_2Xaa_3GAIWRDCK$ (SEQ ID NO: 20), wherein at least one of $Xaa_1$ to $Xaa_3$ is selected from the group consisting of: $Xaa_1$ is selected from tryptophan and alanine; $Xaa_2$ is selected from cysteine and serine; and $Xaa_3$ is selected from arginine and glycine.

In one embodiment of the first aspect of the invention, optionally in combination with any one of the embodiments provided below, the peptide comprises the amino acid sequence $Xaa_1KWWCRXaa_5Xaa_6Xaa_7WRDCK$ (SEQ ID NO: 3), wherein $Xaa_1$, $Xaa_5$, $Xaa_6$ and $Xaa_7$ are each independently any amino acid. In a more particular embodiment, the peptide comprises the amino acid sequence $Xaa_1KWWCRXaa_5Xaa_6Xaa_7WRDCK$ (SEQ ID NO: 3), wherein $Xaa_1$, $Xaa_5$, $Xaa_6$ and $Xaa_7$ are each independently a non-polar amino acid. In an even more particular embodiment, the peptide comprises the amino acid sequence $Xaa_1KWWCRXaa_5Xaa_6Xaa_7WRDCK$ (SEQ ID NO: 3), wherein at least one of $Xaa_1$ to $Xaa_7$ is selected from the group consisting of: $Xaa_1$ is selected from leucine and isoleucine; $Xaa_5$ is selected from glycine and alanine; $Xaa_6$ is selected from glycine and alanine; and $Xaa_7$ is selected from leucine and isoleucine. In an even more particular embodiment, the peptide consists of the amino acid sequence $Xaa_1KWWCRXaa_5Xaa_6Xaa_7WRDCK$ (SEQ ID NO: 3), wherein $Xaa_1$, $Xaa_5$, $Xaa_6$ and $Xaa_7$ are each independently a non-polar amino acid.

In one embodiment of the first aspect of the invention, optionally in combination with any one of the embodiments provided below, the peptide comprises a sequence selected from the group consisting of SEQ ID NO: 4 (LKWWCRGAIWRDCK), SEQ ID NO: 5

(CVYRSGWETYLKWWCRGAIW), SEQ ID NO: 6 (GWETYLKWWCRGAIWRDCKI), SEQ ID NO: 7 (LKWWCRGAIWRDCKILVKTS), SEQ ID NO: 8, SEQ ID NO: 9, and SEQ ID NO: 10.

In a more particular embodiment of the first aspect of the invention, optionally in combination with any one of the embodiments provided below, the peptide consists of a sequence selected from the group consisting of SEQ ID NO: 4 (LKWWCRGAIWRDCK), SEQ ID NO: 5 (CVYRSGWETYLKWWCRGAIW), SEQ ID NO: 6 (GWETYLKWWCRGAIWRDCKI), SEQ ID NO: 7 (LKWWCRGAIWRDCKILVKTS), SEQ ID NO: 8, SEQ ID NO: 9, and SEQ ID NO: 10.

In an even more particular embodiment of the first aspect of the invention, optionally in combination with any one of the embodiments provided below, the peptide comprises the sequence SEQ ID NO: 4, or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 4.

In an even more particular embodiment of the first aspect of the invention, optionally in combination with any one of the embodiments provided below, the peptide consists of the sequence SEQ ID NO: 4, or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 4.

In an even more particular embodiment of the first aspect of the invention, optionally in combination with any one of the embodiments provided below, the peptide comprises the sequence SEQ ID NO: 7, or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 7.

In an even more particular embodiment of the first aspect of the invention, optionally in combination with any one of the embodiments provided below, the peptide consists of the sequence SEQ ID NO: 7, or variant thereof with at least 80%, at least 85%, at least 90%, at least 95%, or at least 99% sequence identity, or a fragment thereof, wherein the variant thereof or the fragment thereof retain the cell-penetrating ability of the sequence SEQ ID NO: 7.

Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. The skilled in the art knows how to test, following routine methods as the ones described in the Examples below, if a variant or a fragment of the sequence retains the cell-penetrating ability. For example, the variant or fragment can be conjugated to a fluorescent cargo and its internalization rate can be compared with the same cargo conjugated with the original sequence, wherein if the internalization rate of the conjugate with the variant or fragment is equal to or higher than the internalization of the conjugate with the original sequence, the variant or fragment retains the cell-penetrating ability of the original sequence.

In the present invention the term "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol. v. 215, pages 403-410.

A summary of the sequences herein described is shown in Table 3:

TABLE 3

| SEQ ID | Amino acid sequence | Name |
|---|---|---|
| Sequences of the invention | | |
| SEQ ID NO: 1 | $Xaa_1KXaa_2WXaa_3Xaa_4Xaa_5Xaa_6Xaa$-W | — |
| SEQ ID NO: 2 | LKWWCRGAIW | — |
| SEQ ID NO: 3 | $Xaa_1KWWCRXaa_5Xaa_6Xaa$-WRDCK | — |
| SEQ ID NO: 4 | LKWWCRGAIWRDCK | Peptide min |
| SEQ ID NO: 5 | CVYRSGWETYLKWWCRGAIW | Peptide 5 |
| SEQ ID NO: 6 | GWETYLKWWCRGAIWRDCKI | Peptide 6 |
| SEQ ID NO: 7 | LKWWCRGAIWRDCKILVKTS | Peptide 7 |
| SEQ ID NO: 8 | LKWWSRGAIWRDCKILVKTS | Peptide 7 C5S |
| SEQ ID NO: 9 | LKAWCRGAIWRDCKILVKTS | Peptide 7 W3A |
| SEQ ID NO: 10 | LKWWCGGAIWRDCKILVKTS | Peptide 7 R6G |
| SEQ ID NO: 19 | $LKXaa_1WXaa_2Xaa_3GAIW$ | — |
| SEQ ID NO: 20 | $LKXaa_1WXaa_2Xaa_3GAIWRDCK$ | — |
| Sequences not forming part of the invention (for comparative purposes) | | |
| SEQ ID | Amino acid sequence | Name |
| SEQ ID NO: 11 | GRKKRRQRRRPQ | TAT |
| SEQ ID NO: 12 | TQITGPTTVNGLERGSLTVQ | Peptide 1 |
| SEQ ID NO: 13 | PTTVNGLERGSLTVQCVYRS | Peptide 2 |
| SEQ ID NO: 14 | GLERGSLTVQCVYRSGWETY | Peptide 3 |
| SEQ ID NO: 15 | SLTVQCVYRSGWETYLKWWC | Peptide 4 |
| SEQ ID NO: 16 | RGAIWRDCKILVKTSGSEQE | Peptide 8 |
| SEQ ID NO: 17 | RDCKILVKTSGSEQEVKRDR | Peptide 9 |
| SEQ ID NO: 18 | LVKTSGSEQEVKRDRVSIKD | Peptide 10 |

In one particular embodiment of the first aspect of the invention, optionally in combination with any one of the embodiments provided below, the length of the peptide is from 10 to 30 amino acid residues, more particularly from 12 to 25 amino acid residues, or even more particularly from 14 to 20 amino acid residues.

In one particular embodiment of the first aspect of the invention, optionally in combination with any one of the embodiments provided below, the length of the peptide is lower than 50, 40, 30, 25 or 20 amino acid residues.

It will be understood by one skilled in the art that the primary amino acid sequence of the peptide of the invention may further be post-translationally modified, such as by glycosylation or phosphorylation, without departing from the invention. Moreover, the N- and/or the C-terminus of the peptide according to the present invention may be chemically modified, for example by addition of chemical groups. Examples of chemical groups, which can be added to the N- and/or the C-terminus of the peptide include the linkers which are described with their amino acid sequences in Table I of Reddy Chichili V P, et al., "Linkers in the structural biology of protein-protein interactions" 2013, Protein Sci. 22:1 53-1 67.

In one particular embodiment of the first aspect of the invention, optionally in combination with any one of the embodiments provided below, the peptide further comprises covalently linked to the N-terminal end of the amino acid sequence a compound selected from the group consisting of an acetyl, a fatty acid, a cholesterol, a poly-ethylene glycol, a nuclear localization signal, a nuclear export signal, a linker, an antibody, a polysaccharide and a targeting molecule.

In one particular embodiment of the first aspect of the invention, optionally in combination with any one of the embodiments provided below, the peptide further comprises covalently linked to the C-terminal end of the amino acid sequence a compound selected from the group consisting of a cysteamide, a cysteine, a thiol, an amide, a carboxyl, a linear or ramified $C_1$-$C_6$ alkyl, a primary or secondary amine, an osidic derivative, a lipid, a phospholipid, a fatty acid, a cholesterol, a poly-ethylene glycol, a nuclear localization signal, a nuclear export signal, a linker, an antibody, a polysaccharide and a targeting molecule.

The peptides of the present invention can be prepared following routine protocols such as by solid phase synthesis, wherein successive steps of (a) deprotecting the amino acid to be bound, and (b) protected-amino acid coupling cycles are performed.

The protecting group can be an N-protecting group, C-protecting group or a side-chain protecting group. There are commercially available protecting groups belonging to all three categories.

Illustrative non-limitative examples of amino acid protecting groups are the N-protecting groups t-Boc (or Boc) and Fmoc. When t-Boc or Fmoc is used in the synthesis of a peptide, the main four steps are: (a) protecting group is removed from the trailing amino acids (commercially available) in a deprotection reaction; (b) deprotection reagents are washed away to provide a clean coupling environment, (c) protected amino acids dissolved in a solvent such as dimethylformamide (DMF) combined with coupling reagents are pumped through the synthesis column, and (d) coupling reagents are washed away to provide clean deprotection environment. Depending on the particular N-protecting group, the deprotection reagent and the coupling reagent is one or another. The skilled person in the art, based on his general knowledge, and by routine methods, can optimize the particular conditions, if necessary.

Alternatively, the peptides of the invention can be obtained by means of recombinant DNA technology.

As above described, the invention also provides a conjugate comprising a peptide or a protein which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid; and a cargo. More particularly, wherein at least one of $Xaa_1$ to $Xaa_7$ is selected from the group consisting of: $Xaa_1$, $Xaa_2$, $Xaa_5$, $Xaa_6$ and $Xaa_7$ are each independently a non-polar amino acid; $Xaa_3$ is a polar-neutral amino acid; and $Xaa_4$ is a basic amino acid. Thus, in the conjugates, the peptide or the protein act as a CPP to facilitate the internalization of cargos to which they are conjugated.

In a further aspect, the invention also provides a conjugate comprising the peptide of the first aspect and a cargo.

All the embodiments above regarding the peptide of the first aspect of the invention are also meant to apply to the second aspect of the invention, in particular all the embodiments regarding the amino acid sequences of the peptide of the invention, which can also form part of the conjugate.

In one particular embodiment of the second aspect of the invention, optionally in combination with any one of the embodiments provided below, the peptide or protein comprises the amino acid sequence $Xaa_1KWWCRXaa_5Xaa_6Xaa_7WRDCK$ (SEQ ID NO: 3), wherein $Xaa_1$, $Xaa_5$, $Xaa_6$ and $Xaa_7$ are each independently any amino acid. More particularly, wherein $Xaa_1$, $Xaa_2$, $Xaa_3$ and $Xaa_4$ are each independently a non-polar amino acid.

In another particular embodiment of the second aspect of the invention, optionally in combination with any one of the embodiments provided below, the peptide or protein comprises the amino acid sequence $LKXaa_1WXaa_2Xaa_3GAIW$ (SEQ ID NO: 19) or $LKXaa_1WXaa_2Xaa_3GAIWRDCK$ (SEQ ID NO: 20), wherein $Xaa_1$, $Xaa_2$, and $Xaa_3$, are each independently any amino acid, particularly, $Xaa_1$ is a non-polar amino acid; and $Xaa_2$ and $Xaa_3$ are each independently a polar amino acid.

In another particular embodiment of the second aspect of the invention, optionally in combination with any one of the embodiments provided below, the conjugate comprises a peptide as defined in the first aspect and a cargo.

In one particular embodiment of the second aspect of the invention, optionally in combination with any one of the embodiments provided below, the peptide or protein comprises a sequence selected from the group consisting of SEQ ID NO: 2, SEQ ID NO: 4, SEQ ID NO: 5, SEQ ID NO: 6, and SEQ ID NO: 7; or alternatively, the protein is CD300f.

In one particular embodiment of the second aspect of the invention, optionally in combination with any one of the embodiments provided below, the peptide or protein is CD300f or a fragment thereof comprising the sequence SEQ ID NO: 2 or the sequence SEQ ID NO: 4.

The term "CD300f" as used herein refers to the protein named CMRF35-like molecule 1, CLM1, IREM-1, IgSF3 or NK inhibitory receptor. The protein sequence from several species is available in several protein databases, such as Uniprot: Q8TDQ1 (CLM1_HUMAN); Q6SJQ7 (CLM1_MOUSE); Q566E6 (CLM1_RAT); or NCBI: NP_620587 (version NP_620587.2).

A "cargo" disclosed herein comprises all the substances that can be transported inside the cell via conjugation with a cell-penetrating peptide, for example, drugs, cosmetics, or active ingredients.

In one particular embodiment of the second aspect of the invention, optionally in combination with any one of the embodiments provided below, the cargo comprises a compound selected from the group consisting of nucleic acid, amino acid, peptide, protein, polysaccharide, lipid, lipoprotein, glycolipid, polymer, small molecule and combinations thereof. In a more particular embodiment, the cargo is selected from a recombinant protein, enzyme, antibody, nanobody, and combinations thereof.

In one embodiment of the second aspect of the invention, optionally in combination with any one of the embodiments provided below, the conjugate comprises a peptide or protein that comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid; or $LKXaa_1WXaa_2Xaa_3GAIW$ (SEQ ID NO: 19), wherein $Xaa_1$, $Xaa_2$, and $Xaa_3$, are each independently any amino acid; and a cargo; with the proviso that the cargo is not an amino acid, peptide, polypeptide or protein.

In one particular embodiment of the second aspect of the invention, optionally in combination with any one of the embodiments provided below, the cargo comprises or consists of a nanovehicle. In a more particular embodiment, the cargo comprises a nanovehicle that is selected from the group consisting of inorganic nanoparticle (e.g. gold nanoparticle or iron-based nanoparticle), micelle, liposome, extracellular vesicle (e.g. microvesicles and exosomes), unilamellar or multilamellar vesicle, nanoemulsion, nanoshell, quantum dot, niosome, dendrimer, and combinations thereof. In a more particular embodiment, the micelle is a polymeric micelle. More particularly, the polymeric micelle is of Poloxamer. Even more particularly, the polymeric micelle is of Poloxamer 407 or Pluronic© F127. In another particular embodiment, the extracellular vesicle is an exosome.

As used herein, a "nanovehicle" refers to microscopic particle whose size is measured in nanometers. A nanovehicle may be loaded with one or more compounds that are liberated once it is internalized by the cell.

A "micelle" is an aggregate of surfactant molecules dispersed in a liquid colloid. A typical micelle in aqueous solution forms an aggregate with the hydrophilic "head" regions or outer side of the micelle in contact with surrounding solvent, sequestering the hydrophobic regions in the inner side of the micelle facing micelle center. A "polymeric micelle" or "micelle polymer" is an organized auto-assembly formed in a liquid and composed of amphiphilic macromolecules, in general amphiphilic di- or tri-block copolymers made of solvophilic and solvophobic blocks. Several micelles that can be used in the conjugates of the invention are described, for example, in the international patent application WO2019129657 of Fundacio Hospital Universitari Vall d'Hebron—Institut de Recerca and Consorcio Centro de Investigacion Biomédica en Red, M.P.

The term "liposome" refers to a spherical vesicle having a lipid monolayer or bilayer. Various examples of liposomes that can be used in the conjugates of the invention are described, for example, in the international patent application WO2014001509 of Consejo Superior De Investigaciones Cientificas (CSIC), Fundació Privada Parc Cientific De Barcelona, Centro De Investigación Biomédica En Red En Bioingenieria, Biomateriales Y Nanomedicina (CIBER-BBN), Fundacio Privada Institut De Recerca Biomédica, Universitat De Barcelona, Fundació Hospital Universitari Vall D'Hebron—Institut De Recerca, Universitat Autónoma De Barcelona.

As used herein, the term "extracellular vesicle" or "EV" refers to a cell-derived vesicle comprising a membrane that encloses an internal space. As used herein the term "exosome" refers to a specific type of EV, which is a cell-derived small (between 40-200 nm in diameter) vesicle comprising a membrane that encloses an internal space, and which is generated from said cell by direct plasma membrane budding or by fusion of the late endosome with the plasma membrane. EVs that can be used in the conjugates of the invention are, for example, the ones described in the international patent application WO2020152298 of of Fundació Hospital Universitari Vall d'Hebron—Institut de Recerca and Consorcio Centro de Investigacion Biomédica en Red, M.P.

In one particular embodiment of the second aspect of the invention, optionally in combination with any one of the embodiments provided below, the cargo comprises a nanovehicle (nanoscale vehicle), which is loaded with one or more therapeutic agents.

The term "therapeutic agent" relates to any compound or mixtures of compounds that are able to promote a therapeutic effect once administered in a "therapeutically effective" amount in an animal, particularly in a mammal, and more particularly in a human. The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

In one particular embodiment of the second aspect of the invention, optionally in combination with any one of the embodiments provided below, the cargo comprises or consists of a nanovehicle which is loaded with one or more therapeutic agents selected from the group consisting of small interfering RNA (siRNA), micro RNA (miRNA), short hairpin RNA (shRNA), long non-coding RNA (LncRNA), a DNA plasmid, an oligopeptide, a protein, a small molecule, and combinations thereof. Depending on the use of the conjugate, the skilled in the art would know which cargo to use.

The conjugate can comprise at least one peptide according to the present invention and at least one cargo molecule. It is also within the present invention that the conjugate comprises more than one peptide or protein according to the present invention, i.e. a plurality of such peptides or proteins, whereby the plurality of the peptides or proteins may comprise a plurality of the same or of different peptides or proteins. Also, the conjugate according to the present invention may also comprise more than one cargo molecule, whereby the plurality of the cargo molecules may comprise a plurality of the same or of different cargo molecules.

In one particular embodiment of the second aspect of the invention, optionally in combination with any one of the embodiments provided below, the peptide and the cargo are conjugated via a covalent bond, optionally mediated by a linker; or a non-covalent bond.

The conjugation of the peptide provided in the present invention can be performed following well-known routine protocols, such as solid phase synthesis or solution selective capping. (Copolovici D. M. et al., "Cell-Penetrating Peptides: Design, Synthesis, and Applications", 2014, ACS Nano, 2014, 8 (3), pp 1972-1994).

In one particular embodiment of the second aspect of the invention, optionally in combination with any one of the embodiments provided below, the cargo is conjugated to the N-terminal or the C-terminal end of the peptide. In a more particular embodiment, the cargo is conjugated via a covalent bond to the N-terminal or the C-terminal end of the peptide.

Such covalent bonds are particularly formed between either suitable reactive group of the peptide and the cargo and, more particularly, between a terminus of the peptide according to the present invention and the cargo. Depending on the chemical nature or the cargo, the moiety, group or radical with which such covalent bond is formed varies and it is within the skills of a person of the art to create such bond.

In one particular embodiment of the second aspect of the invention, optionally in combination with any one of the embodiments provided below, the covalent bond is an amide bond formed between the amine group of the N-terminal amino acid of the peptide with a carboxylic group of the cargo. In another embodiment, the covalent bond is an amide bond formed between the carboxylic group of the C-terminal amino acid of the peptide and an amine group of the cargo.

The bond between the peptide and the cargo of the conjugate may be directly or indirectly, i.e. two components directly adjoin or they may be linked by an additional component of the conjugate, e.g. a spacer or a linker. A linker or spacer may preferably provide further functionalities in addition to linking of the components, and preferably being cleavable, more preferably naturally cleavable inside the target cell, e.g. by enzymatic cleavage. Said spacer may be peptidic or non-peptidic. A non-peptidic spacer can include or may be an ester, a thioester, and a di-sulfide. Examples of linkers are described in Reddy Chichili V P, et al. (supra).

Alternatively, the conjugate can be formed based on non-covalent bond. Such non-covalent bond can be ionic bonds, hydrogen bonds or hydrophobic interaction or a combination of such bonds.

In one particular embodiment of the second aspect of the invention, optionally in combination with any one of the embodiments provided below, the non-covalent bond is formed by a stretch of lysine residues attached by covalent bonds to a peptide according to the present invention, and the phosphate backbone of an oligonucleotide. More particularly, the stretch of lysine consists of about 5 to 15 lysine residues.

In one particular embodiment of the second aspect of the invention, optionally in combination with any one of the embodiments provided below, the peptide or the protein is of a length lower than 500 amino acid residues, lower than 400 amino acid residues, lower than 300 amino acid residues, lower than 250 amino acid residues, lower than 200 amino acid residues, or lower than 100 amino acid residues. In a more particular embodiment, the peptide or the protein is of a length from 10 to 300 amino acid residues, or from 14 to 250 amino acid residues.

The invention also provides a conjugate comprising a cell-penetrating peptide which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid, in particular which comprises the amino acid sequence $LKXaa_1WXaa_2Xaa_3GAIW$ (SEQ ID NO: 19), wherein $Xaa_1$, $Xaa_2$, and $Xaa_3$, are each independently any amino acid; and a cargo.

The invention also provides pharmaceutical composition comprising a therapeutically effective amount of a conjugate as defined the second aspect with at least one pharmaceutically acceptable excipient, diluent or carrier.

All the embodiments of the conjugate of the second aspect are also meant to apply to the pharmaceutical composition of the third aspect.

The expression "pharmaceutical composition" encompasses both compositions intended for human as well as for non-human animals.

The expression "therapeutically effective amount" as used herein, refers to the amount of the peptide or conjugate that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipient, diluent or carrier" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavoring agents can be present in the composition, according to the judgment of the formulator.

The pharmaceutical compositions containing the peptide or the conjugate of the invention can be presented in any dosage form, for example, solid or liquid, and can be administered by any suitable route, for example, oral, parenteral, rectal, topical, intranasal, intraocular, intraperitoneal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable hydrogels, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As above mentioned, the invention also provides in a fourth aspect the conjugate of the second aspect or the pharmaceutical composition of the third aspect for use as a medicament.

In a particular embodiment of the second, third, and fourth aspects, optionally in combination with any of the embodiments provided above or below, the cargo comprises a therapeutic agent.

In a particular embodiment of the fourth aspect, optionally in combination with any of the embodiments provided above or below, the conjugate or the pharmaceutical composition is for use in the treatment or the prevention of a condition selected from the group consisting of neoplastic disease, immune disease, cardiovascular disease, neurological disease, inflammatory disease, lysosomal disease, and infection. In a more particular embodiment, the conjugate or the pharmaceutical composition is for use in the treatment or the prevention of a neoplastic disease. This aspect can also be formulated as the use of the conjugate or the pharmaceutical composition of the invention for the manufacture of a medicament for the treatment or prevention of a neoplastic disease, immune disease, cardiovascular disease, neurological disease, inflammatory disease, lysosomal disease, and infection; more in particular a medicament for the treatment or prevention of a neoplastic disease. This aspect can also be formulated as a method for treating or preventing a neoplastic disease, immune disease, cardiovascular disease, neurological disease, inflammatory disease, lysosomal disease, and infection, more in particular method for treating or preventing a neoplastic disease, the method comprising administering a therapeutically effective amount of the conjugate or the pharmaceutical composition of the invention to a subject in need thereof.

The skilled in the art would know which cargos should be used in the conjugate of the invention depending on the disease to be treated. For instance, when the conjugate or the pharmaceutical composition of the invention is for the treatment or prevention of a neoplastic disease, the cargo may be a chemotherapeutic agent, or alternatively, a nanovehicle loaded with a chemotherapeutic agent. The term "chemotherapeutic agent" is used herein refers to an agent or drug that inhibits tumor cell growth and/or induces tumor cell death. Chemotherapeutic agents include, but are not limited to, platinum derivatives (e.g., cisplatinum and carboplatinum), taxanes (e.g., paclitaxel), steoid derivatives, anti-metabolites (e.g., 5-fluorouracil, methotrexate and cytosine arabinoside), plant alkaloids (e.g., vindesine VP16, vincristine and vinblastine), antibiotics (e.g., adriamycin, mitomycin C, bleomycin, mithramycin, daunorubicin, mitoxantrone, and doxorubicin), etoposide, arsenic derivatives, intercalating agents, alkylating agents (e.g., melphalan, cyclophosphamide, chlorambucil, busulphan, thiotepa, isofamide, mustine, and the nitrosoureas), enzymes (e.g., asparaginase), biological response modifiers (e.g., immunoadjuvants and immunorestoratives), hydroxyurea, procarbazine, and combination thereof.

Surprisingly, as shown in Example 4 below, the CPPs of the present invention are capable of delivering cargos to the highly resistant and malignant cancer stem cell (CSC) subpopulation, thereby allowing the efficient treatment of cancer. As used herein, "cancer stem cells" or "CSC" are a subpopulation of cells within tumors with capabilities of self-renewal, differentiation, and tumorigenicity when transplanted into an animal host. A number of cell surface markers such as CD44, CD24, and CD133 are often used to identify and enrich CSCs.

Thus, in a particular embodiment of the fourth aspect, optionally in combination with any of the embodiments provided above or below, the conjugate or the pharmaceutical composition of the invention is for use in the treatment or the prevention of a neoplastic disease through the delivery of the cargo into CSC. In other words, the conjugate or the pharmaceutical composition of the invention are useful for targeting CSC in methods of treating cancer. Thus, in a more particular embodiment of the fourth aspect, optionally in combination with any of the embodiments provided above or below, the conjugate or the pharmaceutical composition of the invention is for use in targeting CSC in the prevention or treatment of a neoplastic disease. As used herein, "targeting CSC" refers to the specific elimination of CSCs through the delivery into their cytoplasm of cytotoxic agents. In the conjugates of the invention, the cytotoxic agent is present in the cargo.

As used herein, the term "neoplastic disease" refers to cancers of any kind and origin and precursor stages thereof. Illustrative non-limiting examples of neoplastic diseases which can be treated with the conjugate and pharmaceutical composition of the invention include, although they are not limited to, papillomas, adenomas, lipomas, osteomas, myomas, angiomas, nevi, mature teratomas, carcinomas, sarcomas.immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocarcinoma, head and neck cancer, etc.

As above described, in a fifth aspect the conjugate or the pharmaceutical composition of the invention are for use in diagnosis and/or prognosis.

In a particular embodiment of the second, third, fourth and fifth aspects, optionally in combination with any of the embodiments provided above or below, the cargo comprises a labelling agent.

In the present invention, the term "labelling agent" refers to any component that specifically determines the presence of a given component inside a cell, or, more specifically, a biomarker.

A list of suitable labelling agents includes, without limitation, fluorescent dyes, radioisotopes, enzymes and antibodies that can be either independently detected or detected in conjunction with the addition of a substrate or other molecule that reacts therewith.

As mentioned above, in a sixth aspect, the invention provides an in vitro method for delivering a cargo into a cell, the method comprising administering the conjugate as defined in the second aspect or the pharmaceutical composition as defined in the third aspect to a cell. The embodiments of the first, second and third aspects of the invention are meant to apply to this sixth aspect.

In a particular embodiment of the sixth aspect, optionally in combination with any of the embodiments provided above or below, the method comprising administering to a cell the conjugate as defined in the second aspect; the pharmaceutical composition as defined in the third aspect, or a conjugate comprising a peptide or a protein which comprises the amino acid sequence LKXaa1WXaa2Xaa3GAIW (SEQ ID NO: 19), wherein Xaa1, Xaa2, and Xaa3, are each independently any amino acid, and a cargo.

In a particular embodiment of the sixth aspect, optionally in combination with any of the embodiments provided above or below, the cell is a cancer cell. In an even more particular embodiment, the cell is a cancer stem cell (CSC).

As mentioned above, in a seventh aspect, the invention provides a polynucleotide which encodes the peptide as defined in the first aspect. In a particular embodiment of the seventh aspect, optionally in combination with any of the embodiments provided above and below, the polynucleotide is DNA or RNA.

As mentioned before, in an eighth aspect, the invention provides a vector comprising the polynucleotide of the seventh aspect. Examples of suitable vectors include those conventionally used in biomedicine and known to the skilled person.

As mentioned above, in a ninth aspect, the invention provides a host cell which is transformed or transfected with the polynucleotide or the vector of the invention. The skilled person would know which host cells are suitable for the synthesis of the protein of the invention.

As mentioned before, in a tenth aspect the invention provides a cell culture comprising the host cell of the ninth aspect. Examples of suitable cell culture mediums and conditions include those conventionally used in cell biology and known to the skilled person.

As above mentioned, in an eleventh aspect, the invention provides process for the production of the peptide according to the first aspect. The skilled person is familiar with several standard methods to isolate the resulting peptide from the cell culture or after in vitro transcription and/or translation, for instance, Protein A purification column purification.

As described before, in a twelfth aspect the invention provides a process for the production of the conjugate as defined in the second aspect. The skilled person is well aware of suitable reaction conditions for conjugating the peptide or protein to the cargo (Copolovici D. M, supra).

As above described, in a fourteenth aspect the invention provides the use of a peptide or protein which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4$ $Xaa_5$, $Xaa_6$ and $Xaa_7$ are each independently any amino acid as a cell-penetrating peptide for transporting a cargo inside a cell in vitro, wherein the peptide is conjugated to the cargo.

The embodiments of the first and second aspect of the invention are meant to apply to this fourteenth aspect.

In a particular embodiment of the fourteenth aspect of the invention, optionally in combination with any of the embodiments provided above or below, the peptide is of a length from 10 to 50 amino acid residues, and the protein is of a length from 51 to 400 amino acid residues.

In a particular embodiment of the fourteenth aspect of the invention, optionally in combination with any of the embodiments provided above or below, the peptide or protein comprises the amino acid sequence $LKXaa_1WXaa_2Xaa_3GAIW$ (SEQ ID NO: 19), wherein $Xaa_1$, $Xaa_2$, and $Xaa_3$, are each independently any amino acid, as a cell-penetrating peptide for transporting a cargo inside a cell, wherein the peptide or protein is conjugated to the cargo.

As mentioned before, in a fifteenth aspect the invention provides a process for the production of a conjugate comprising a peptide as defined in the first aspect and a extracellular vesicle cargo, the process comprising (a) culturing a host cell as defined in the ninth aspect under suitable conditions, and (b) isolating the resulting conjugate formed by the peptide conjugated to the extracellular vesicle of the host cell.

The skilled in the art would know how to adjust the expression levels of the peptide in the host cell following routine techniques in molecular biology, in order to allow the conjugation of the peptide to the natural extracellular vesicles produced by the host cell.

Thus, in a particular embodiment of the fifteenth aspect, optionally in combination with any of the embodiments provided above or below, the host cell overexpresses the peptide. As used herein, "overexpression" refers to the expression of a particular gene sequence in which the production of mRNA or protein or peptide in a transgenic organism exceeds the physiological levels of production in non-transgenic organism.

In a further aspect the invention provides a process for the production of a conjugate as defined in the second aspect, wherein the cargo is an extracellular vesicle (EV), the process comprising (a) culturing a host cell expressing the peptide or protein, and producing the extracellular vesicle, under suitable conditions, and (b) isolating the resulting conjugate formed by the peptide or protein conjugated to the extracellular vesicle of the host cell. In a more particular embodiment, the host cell overexpresses the peptide or protein.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

For reasons of completeness, various aspects of the invention are set out in the following numbered clauses:

Clause 1. A peptide of a length from 10 to 50 amino acid residues, which comprises the amino acid sequence $Xaa_1KXaa_2WXaa_3Xaa_4Xaa_5Xaa_6Xaa_7W$ (SEQ ID NO: 1), wherein $Xaa_1$, $Xaa_2$ $Xaa_3$, $Xaa_4Xaa_5$, $Xaa_6$ and $Xaa_7$ are each independently any amino acid.

Clause 2. The peptide according to clause 1, wherein at least one of $Xaa_1$ to $Xaa_7$ is selected from the group consisting of:

$Xaa_1$, $Xaa_2$, $Xaa_5$, $Xaa_6$ and $Xaa_7$ are each independently a non-polar amino acid;

$Xaa_3$ is a polar-neutral amino acid; and $Xaa_4$ is a basic amino acid.

Clause 3. The peptide according to any of clauses 1 or 2, wherein at least one of $Xaa_1$ to $Xaa_7$ is selected from the group consisting of:

$Xaa_1$ is selected from leucine and isoleucine;

$Xaa_2$ is selected from tryptophan and alanine;

$Xaa_3$ is selected from cysteine and serine;

$Xaa_4$ is selected from arginine and glycine;

$Xaa_5$ is selected from glycine and alanine;

$Xaa_6$ is selected from glycine and alanine; and $Xaa_7$ is selected from leucine and isoleucine.

Clause 4. The peptide according to any of clauses 1-3, which comprises the amino acid sequence $Xaa_1$KWWCR$Xaa_5Xaa_6Xaa_7$WRDCK (SEQ ID NO: 3), wherein $Xaa_1$, $Xaa_5$, $Xaa_6$, and $Xaa_7$ are each independently any amino acid.

Clause 5. The peptide according to any of clauses 1-4, which comprises a sequence selected from the group consisting of SEQ ID NO: 4, SEQ ID NO: 5, SEQ ID NO: 6, and SEQ ID NO: 7.

Clause 6. A conjugate comprising:

a peptide or a protein which comprises the amino acid sequence $Xaa_1$K$Xaa_2$W$Xaa_3Xaa_4Xaa_5Xaa_6Xaa_7$W (SEQ ID NO: 1), wherein $Xaa_1$, $Xaa_2$ $Xaa_3$, $Xaa_4$ $Xaa_5$, $Xaa_6$ and $Xaa_7$ are each independently any amino acid; and a cargo.

Clause 7. The conjugate according to clause 6, wherein the cargo comprises a compound selected from the group consisting of nucleic acid, amino acid, peptide, protein, polysaccharide, lipid, lipoprotein, glycolipid, small molecule and combinations thereof.

Clause 8. The conjugate according to any of clauses 6-7, wherein the cargo comprises a nanovehicle selected from the group consisting of micelle, liposome, extracellular vesicle, nanoemulsion, nanoshell, quantum dot, niosome, dendrimer, inorganic nanoparticle, and combinations thereof.

Clause 9. The conjugate according to any of clauses 6-8, wherein the peptide or protein and the cargo are conjugated via:

a covalent bond, optionally mediated by a linker; or alternatively, a non-covalent bond.

Clause 10. A pharmaceutical composition comprising a therapeutically effective amount of a conjugate as defined in any of clauses 6-9 with at least one pharmaceutically acceptable excipient, diluent or carrier.

Clause 11. The conjugate as defined in any of clauses 6-9 or the pharmaceutical composition as defined in clause 10 for use as a medicament.

Clause 12. The conjugate or the pharmaceutical composition for use according to clause 11, which is for use in targeting cancer stem cells in the prevention or treatment of a neoplastic disease.

Clause 13. The conjugate as defined in any of clauses 6-9 or the pharmaceutical composition as defined in clause 10 for use in diagnosis and/or prognosis.

Clause 14. An in vitro method for delivering a cargo into a cell, the method comprising administering the conjugate as defined in any of clauses 6-9 or the pharmaceutical composition as defined in clause 10 to a cell.

Clause 15. A polynucleotide which encodes the peptide as defined in any of clauses 1 to 5.

EXAMPLES

Example 1: Screening of Peptides Sequences for Membrane Lipids Interaction

In an attempt to identify the sites of interaction of CD300f with Sphingomyelin (SM), the inventors performed a peptide-based epitope mapping approach. 24 overlapping, 20mer peptides were designed with a 15-aa overlap between successive peptides covering the Ig and stem extracellular sequences of human CD300f. It was analyzed whether any of those 24 peptides could inhibit binding of CD300f to plastic-immobilized SM. Only three of them, peptides 5 (SEQ ID NO:5), 6 (SEQ ID NO:6) and 7 (SEQ ID NO:7), which contained the sequence LKWWCRGAIW (SEQ ID NO: 2), inhibited binding upon co-incubation with CD300f-Ig (see FIG. 1).

The absence of an aspartic acid in the sequence covered by peptides 5, 6 and 7 as well the fact that contains the residue tryptophan 55 plus to additional tryptophan residues (W56 and W62) suggest that this region of the Ig domain of CD300f could be involved in the binding to the nonpolar surface of SM. This data suggests that the sequence LKWWCRGAIW present in the Ig domain of CD300f is able to bind the acyl chains of Sphingomyelin.

Figure 2:
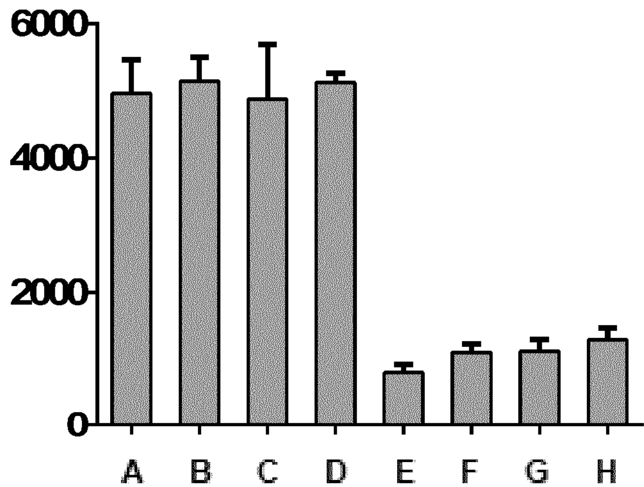
FIG. 2, related to Example 1, is a bar diagram showing the binding capacity of the indicated peptides to sphingomyelin (SM). They y-axis represents absorbance (%). "A" represents the control; "B" represents DMSO; "C" represents Peptide 1; "D" represents Peptide 2; "E" represents Peptide 7; "F" represents Peptide 7 C5S (SEQ ID NO: 8); "G" represents Peptide 7 W3A (SEQ ID NO: 9); and "H" represents Peptide 7 R6G (SEQ ID NO: 10).

Moreover, different amino acids of the sequence LKWWCRGAIW (SEQ ID NO: 2) were mutated to try to map the interaction with the phospholipid. The mutation of the tryptophan residue in position three, the cysteine residue in position five, or the arginine residue in position six did not alter the binding capacity of the sequence, suggesting that none of these amino acids seems to participate in the interaction (see FIG. 2).

Example 2: Peptides Conjugation into Polymeric Micelles Surface and Cell Internalization Assessment Methods F127:COOH Synthesis by the Maleic Anhydride Method:

The correct stoichiometry for this reaction was calculated from the literature, being 11 the ratio of maleic anhydride over polymer. F127 and maleic anhydride were dissolved in distilled $CHCl_3$ and the solution was allowed to react for 24 h under stirring at 70° C. in a condensation system to avoid any loss of solvent. The solution was concentrated and poured twice into an excess amount of iced cold diethyl ether to precipitate the reaction product. Then, F127-COOH was dried under vacuum dehydration and collected as white powder.

F127:COOH Polymers Characterization:

After synthesis, each batch of polymers were characterized through FT-IR and $^1$H-NMR analysis. FT-IR was carried out in Characterization of Soft-Materials Services at Institut de Ciéncia de Materials de Barcelona (ICMAB-CSIC) using a spectrometer Perkin-Elmer Spectrum One (energy range: 450-4000 $cm^{-1}$) equipped with a Universal Attenuated Total Reflectance accessory (U-ATR). $^1$H-NMR analyses have been carried out in Nuclear magnetic resonance service (SeRMN) of the Universitat Autónoma de Barcelona (UAB) using a spectrometer Avancelll-400nb.

Conjugation of F127 with 5-DTAF:

Fluorescent F127 was synthesized through covalent conjugation of Pluronic® F127 (Sigma Aldrich, Spain) with 5-DTAF (Sigma Aldrich, Spain) in an aqueous medium via nucleophilic aromatic substitution by an addition-elimination pathway, as previously described (Andrade, F., et al., "Biological assessment of self-assembled polymeric micelles for pulmonary administration of insulin", 2015, Nanomedicine, vol. 11(7), pp. 1621-31). Briefly, a stock solution of 20 g/L 5-DTAF in DMSO was diluted in 0.1M sodium bicarbonate (pH 9.3) and added to a 6% (w/v) F127 solution in 0.1M sodium bicarbonate (pH 9.3) to a final molar ratio of 1:2 (F127:5-DTAF). The reaction proceeded overnight in the dark at RT. The labeled polymer was purified from the excess of unreacted 5-DTAF by dialysis (12,000-14,000 MWCO Spectra/Por® membrane from Spectrum Europe BV, The Netherlands) against Type I ultrapure water. The dialyzed polymer solutions were lyophilized and stored in closed containers protected from light.

F127:F127:COOH Micelles Preparation:

Polymeric micelles (PM) were prepared using the film hydration technique. Briefly, the polymers were individually weighted and dissolved in a mixture of methanol:ethanol (1:1). Then, the solvent was removed under vacuum in a rotary evaporator and the formed film was left to dry overnight at room temperature to eliminate any remaining solvent. The film was then hydrated with PBS and vortexed during 5 minutes. For the PM functionalization with the different peptides, an adequate amount of EDC [1-Ethyl-3-(3-dimethylaminopropyl)carbodiimide] was added to the rehydration solution and incubated with the formulation during 30 minutes. Afterward, the peptides solutions were added and incubated under stirring 2 hours at RT.

Micelles Physicochemical Characterization:

Particles mean hydrodynamic diameter (md) and polydispersity index (Pdi) were measured by dynamic light scattering (DLS) and zeta potential was assessed by laser doppler micro-electrophoresis using a NanoZS measurement range of 0.3 nm-10.0 microns and sensitivity of 0.1 mg/mL (Malvern Instruments, UK). For each formulation, at least three batches were produced and analyzed using MiliQ water as solvent for dilution of the PM. Particle shape and morphology were observed by transmission electron microscopy (TEM) analyses performed at the Electron Microscopy Service at ICMAB, Barcelona using the 120 kV JEOL 1210 TEM, which have a resolution point of 3.2. Gatan software was used to process information and get measures form TEM images.

Cell Culture Conditions:

MCF-7 (ATCC number HTB-22) breast cancer cell line and HCT116 (ATCC number CCL-247) colon cancer cell line were obtained from American Type Culture Collection (ATTC, LGC Standards, Barcelona, Spain). The cells were cultured in RPMI medium supplemented with 10% FBS, 1% penicillin-streptomycin, 1% L-glutamine, 1% non-essential amino acids and 1% of sodium pyruvate. The cells were maintained at 37° C. under 5% CO2 saturated atmosphere. The medium was changed every other day and, upon confluence, cells were harvested from plates with 0.25% trypsin-EDTA to be passed to other plates to continue expansion, be frozen or used in in vitro studies.

Micelles Internalization:

Flow cytometry was used to verify the internalization of 5-DTAF-fluorescently labeled PM in MCF-7 and HCT116 cell lines. For the quantitative fluorescence-activated cell sorting (FACS), $2\times10^4$ cells were seeded in complete medium in 96 well plates for 24 hours to allow adhesion. Micelles were added to cells at different time points and then harvested and re-suspended in PBS supplemented with 10% FBS and DAPI (1 μg/mL) used for vital staining. The plate was analyzed in a cytometer Fortessa (BD Biosciences, USA). Data was analyzed with FCS Express 4 Flow research edition software (De Novo Software, Los Angeles, USA). Forward and side scatter gating removed contaminants. For each sample, at least 10000 individual cells were collected and the mean fluorescence intensity was evaluated.

Results

In order to understand the utility of the peptides of the invention as CPP, Pluronic© F127 based PM (polymeric micelles) were functionalized with different CD300f peptides through covalent bond between the peptides terminal amines and the carboxylic terminals of the polymers. Pluronic© F127 presents free alcohol groups in each end of the chain that were previously transformed into carboxylic groups through the maleic anhydride method. This transformation was confirmed by FT-IR and $^1$H-NMR. The appearance of a peak at 1725 cm-indicated the formation of carbonyl group, which belongs to the carboxylic acid of modified F127. The conjugation of peptides into the formed carboxylic groups was subsequently mediated by EDC activation.

Three different CD300f peptides comprising the LKWWCRGAIW sequence were tested: peptide 6 (SEQ ID NO:6), peptide 7 (SEQ ID NO:7), and peptide min (SEQ ID NO: 4). For comparative purposes, a CD300f peptide that does not comprise SEQ ID NO: 2, peptide 10 (SEQ ID NO:18) was also tested. The whole CD300f protein was also tested as CPP.

All the peptides as well as the CD300f protein were conjugated (1 mg/ml final concentration in the micelles) onto the surface of 5-DTAF labelled (green fluorescent) micelles and their internalization at different time-points assessed in MCF-7 and HCT116 breast and colon cancer cell lines, respectively. As a positive control the cell penetrating peptide TAT was also conjugated into the micelles surface, while no conjugated micelles were used as negative control.

Figure 3:
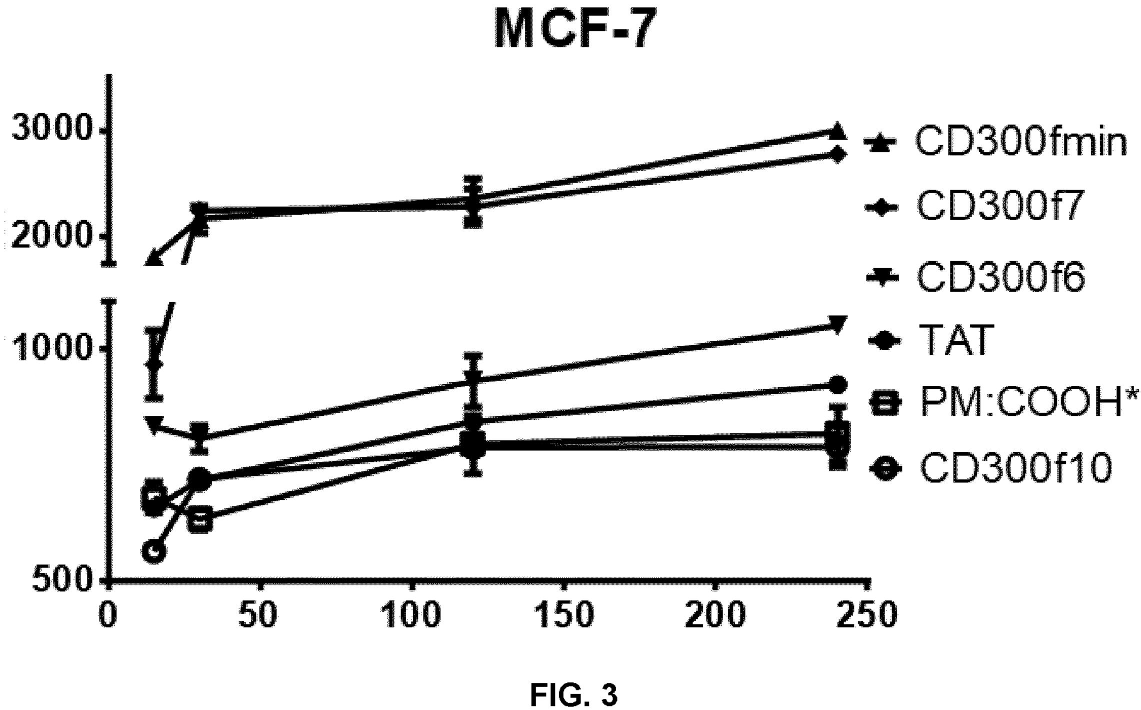
FIG. 3, related to Example 2, is a diagram showing the cell internalization rates of polymeric micelles conjugated to the indicated peptides in MCF-7 cells. The y-axis represents fluorescence intensity (F.U.) (Mean±SEM) and the x-axis represents the time (min). "CD300fmin" corresponds to Peptide min (SEQ ID NO: 4); "CD300f7" corresponds to Peptide 7 (SEQ ID NO: 7); "CD300f6" corresponds to Peptide 6 (SEQ ID NO: 6); "TAT" corresponds to SEQ ID NO: 11; "PM:COOH" corresponds to micelles control; "CD300f10" corresponds to Peptide 10 (SEQ ID NO: 18)
Figure 4:
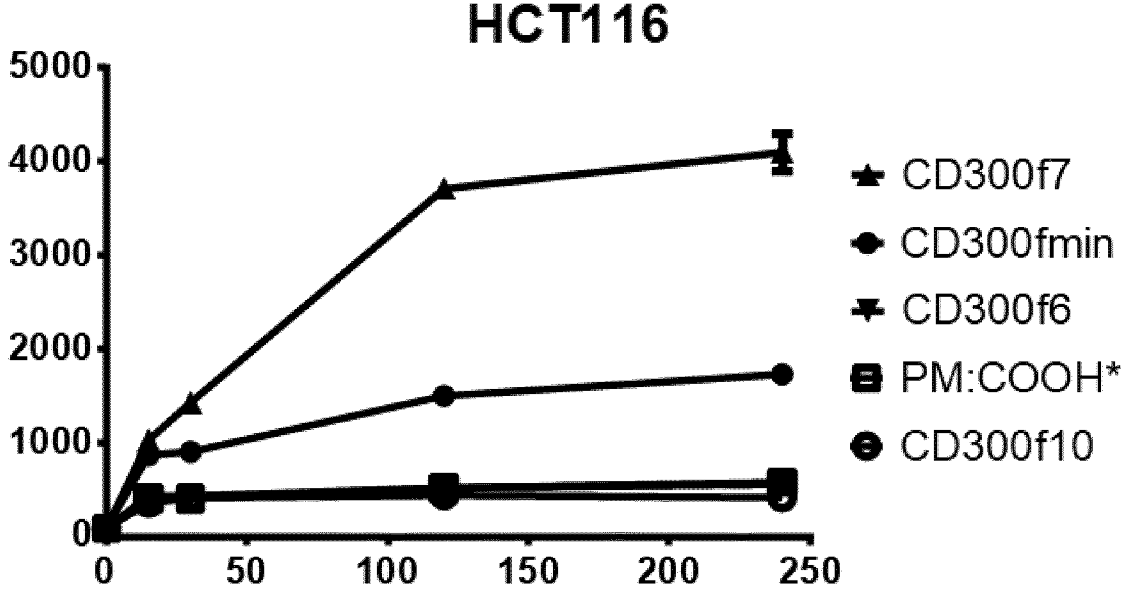
FIG. 4, related to Example 2, is a diagram showing the cell internalization rates of polymeric micelles conjugated to the indicated peptides in HCT116 cells. The y-axis represents fluorescence intensity (F.U.) (Mean±SEM) and the x-axis represents the time (min). The peptides assayed are as indicated in FIG. 3.
Figure 5:
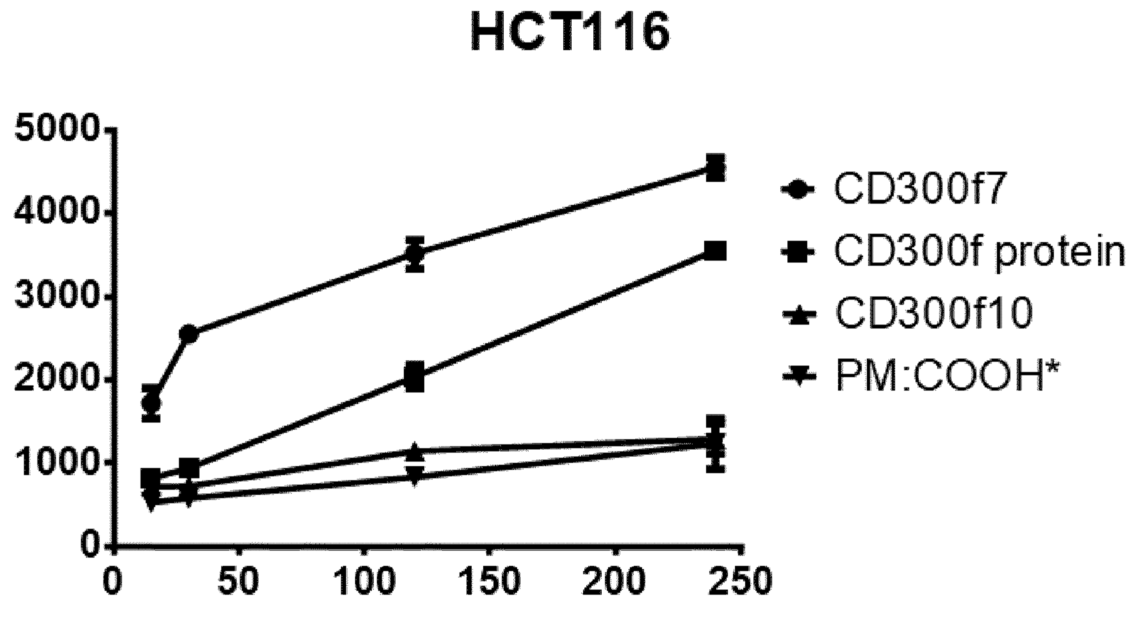
FIG. 5, related to Example 2, is a diagram showing the cell internalization rates of polymeric micelles conjugated to the indicated peptides in HCT116 cells. The y-axis represents fluorescence intensity (F.U.) (Mean±SEM) and the x-axis represents the time (min). The peptides assayed are as indicated in FIG. 3.

The obtained results demonstrate a clear improved and faster internalization for the particles functionalized with the peptides comprising the LKWWCRGAIW sequence (FIGS. 3, 4 and 5). More importantly, the improvement in the internalization is much stronger than the one obtained with the gold standard CPP-TAT (FIG. 3). This results show that, surprisingly, the peptides of the invention and the protein CD300f are better CPPs than the ones currently available in the market.

Example 3: Peptides Conjugation onto Extracellular Vesicle (EV) Surface and Cell Internalization Assessment Methods Extracellular Vesicles (EVs) Synthesis and Purification.

EVs (Ø) were isolated from supernatants (SNs) of HeLa cells cultured in monolayer at 70-80% confluency. SNs containing EVs were generated by the incubation during 48 h of cells with EV production media, namely, regular RMPI supplemented with EV depleted FBS (ThermoFisher Scientific, REF: A2720801) (10% v/v), L-Glutamine and Penicillin-Streptomycin antimicrobial cocktail.

Cell debris and big microvesicles were removed from SNs by consecutive centrifugation rounds at increasing speeds as follows: 1$^{st}$ Round 300 g, 10 min, 2$^{nd}$ Round 2000 g, 10 min and 3$^{rd}$ Round 10000 g, 30 min. Then SNs were concentrated by using VIVASpin (Sartorius) devices with a filter pore size of 300 KDa, allowing at the same time to remove free protein from the sample, 7000 g and 15 min and following manufacturer's instructions. Additional concentration cycles were performed until achieving a concentration factor of 50×. At this point, samples were washed three times by diluting EVs in PBS, 1:10 and concentrating the sample again as described above. All centrifugation steps were carried out at 4° C.

The same protocol using HeLa cells stably transfected with a CD300f expression vector was performed in order to isolate CD300f functionalized EVs [EVs (CD300f)].

EVs Quantification

EVs or cell lysates were prepared by diluting EVs samples 1:5 in CelLytic™ MT Cell Lysis Reagent (Sigma, REF: C3228-50 ML) and total protein amount was determined by BCA Pierce™ (ThermoFisher Scientific, REF: 23227) method following manufacturer's instructions. Total protein amount was used as reference for EV quantity in further studies.

F7 Peptide (SEQ ID NO:7) Conjugation.

The F7 peptide (SEQ ID NO:7) was conjugated onto EV surface (EVs (0)+F7) following the same protocol as described above in Example 2 for polymeric micelles.

Briefly, —COOH groups from proteins on the EV surface were activated by the incubation with EDC [1-Ethyl-3-(3-dimethylaminopropyl)carbodiimide] at 0.14 mg/mL (final concentration), 30 min at RT and thoroughly mixed with a magnetic stirrer. Then, peptide F7 was added at 1 mg/mL and further incubated for 3 h at room temperature (RT). Finally, in order to remove unbound peptide, samples were dialyzed using 100 KDa cassettes, overnight at 4° C.

EVs DiD Labeling

EVs were incubated to a concentration of 100 μg/mL with DiD (ThermoFisher Scientific, REF: D7757) for 30 min at 37° C. Dye excess was removed by dialysis in a Slide-A-Lyzer™ MINI Dialysis Device, 3.5K MWCO, 0.1 mL (Thermo Scientific) against PBS, overnight at 4° C., following manufacturer's instructions.

EV Internalization Assay.

EV internalization capability was determined by complementary quantitative fluorescence-activated cell sorting (FACS) and confocal microscopy techniques.

Flow cytometry: $4\times10^4$ cells of either HCT116 or MDA-MB-231 were seeded in 96 well and cultured for 24 hours. 2.5 μg EVs/mL of DiD labeled EVs produced as described above were added to cells and incubated for 15, 30, 60 and 240 min. Cells were detached by trypsin digestion, 0.05% (w/v) and neutralized in complete RPMI medium supplemented with DAPI (1 μg/mL final concentration), in order to remove dead cells from analysis. Cell fluorescence intensity was analyzed in a LSR Fortessa flow cytometer (Beckton Dickinson). Data was further processed using FCS express 4 software (De novo software) and % of fluorescent cells represented.

Confocal Microscopy: $8\times10^4$ cells of either HCT116 or MDA-MB-231 cells were seeded in an 8 chambered coverglass (Lab-Tek®II, Eppendorf) and incubated 24 h at 37° C. and 5% $CO_2$. Then, 6 μg/well of DiD labeled EVs produced as described above were incubated for 4 h and cell membranes were counterstained with 5 μg/mL Cell Mask™ (green), 10 min at 37° C. Samples were fixed in 4% paraformaldehyde (PFA). Image acquisition was carried out by spectral confocal microscopy Zeiss LSM 980 and further processed using ImageJ software (NIH).

Cell Viability Assay.

EV and EV derivatives toxicity was assessed by MTT assay (VWR, REF: 0793-5G) in HCT116 cells following manufacturer's instructions. Briefly, cells were challenged with 3 distinct concentrations: 50 μg/mL, 5 μg/mL and 0.5 μg/mL, and incubated for 72 h. Then, 10 μL of MTT reagent (3-(4,5-Dimethylthiazol-2-yl)-2,5-Diphenyltetrazolium Bromide) at 5 mg/mL were added per well and further incubated for 4 h at 37° C. After incubation cell culture medium was removed and formazan crystals dissolved in DMSO. Colorimetric determination was performed at 590 nm in a Biotek ELx800 plate reader. Cell viability was represented as the relative value with respect to non-treated controls.

Results

Figure 6:
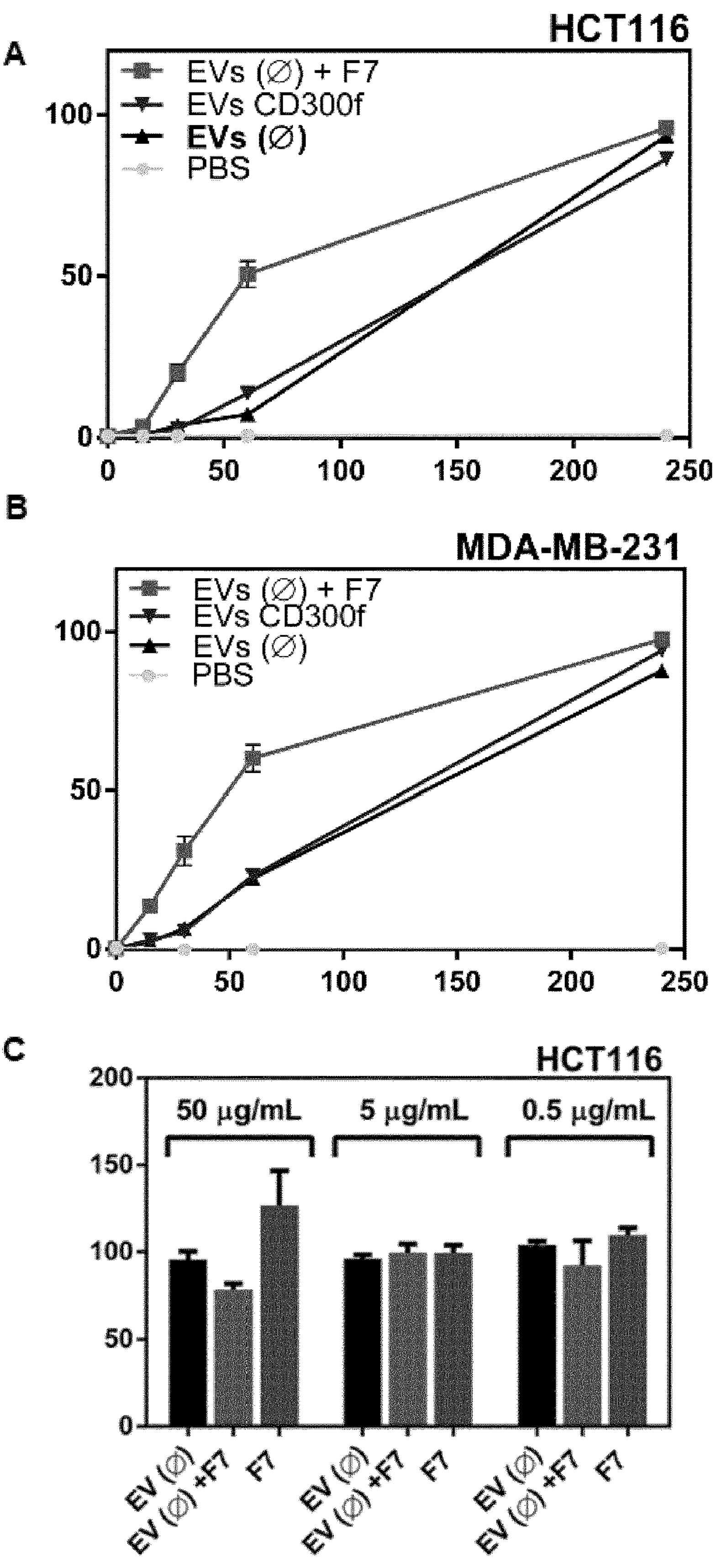
FIG. 6, related to Example 3, shows the internalization efficiency and toxicity of EVs conjugated to the peptides of the invention. A and B show the internalization profile of DiD labeled EVs along the time monitored by FACS in HCT116 cells (A) and MDA-MB-231 cells (B). The y-axis represents Fluorescent cells (%) (Mean±SEM); x-axis represents Time in minutes. C is a bar diagram showing relative cell viability of HCT116 cells after a challenge with 50, 5, and 0.5 μg/mL of the indicated compound. The y-axis represent % Cell Viability (Mean±SEM). "EV (0)" corresponds to cells treated with EVs not conjugated; "EV (0)+FT" treated with EVs conjugated to peptide 7 (i.e. peptide F7) (SEQ ID NO:7); "EV CD300f" treated with EVs conjugated to the CD300f protein; "F7" treated with the free peptide 7 (SEQ ID NO:7); and "PBS" treated with PBS.

EVs isolated from HeLa cells and conjugated to the peptide F7 (SEQ ID NO:7) exhibited significantly higher internalization capacity than nude EVs (0) but also than EVs displaying CD300f, for both HCT116 colorectal cancer and MDA-MB-231 triple negative breast cancer cell lines (FIGS. 6 A and B). Flow cytometry profiles this behavior more markedly at shorter incubation times, up to 1 h. Additionally, confocal imaging confirmed superior cell membrane penetration capacity of F7 functionalized EVs (figure not shown).

Finally, assessing EVs (0)+F7 conjugate potential toxicity non-significant differences were detected at the 3 tested concentrations for any of the conditions in HCT116 cells indicating that enhanced EV uptake was not detrimental for cell survival (FIG. 6 C). These results further demonstrate that the peptides of the invention are an efficient and safe tool to deliver cargos inside cells.

Example 4: Internalization Study in Cancer Stem Cells (CSC) Versus Non Cancer Stem Cells (Non-CSC)

CSC Isolation

The MDA-MB-231 stably expressed an ALDH1A1/tdTomato reporter vector. Consequently, CSC expressed tdTomato (red fluorescence) driven by the CSC specific promoter (ALDH1A1), while Non-CSC did not show tdTomato fluorescence. This system offered a permanent CSC tagging which permitted the identification and separation of CSC from heterogeneous populations. The CSC nature of tdTomato positive cells was previously confirmed by expression of stemness markers, tumorspheres formation and high in vivo tumorigenic capacity.

PM Internalization

MDA-MB-231 ALDH1A1:tdTomato cells were sorted by FACS (FACSAria, BD Biosciences) in order to obtain highly pure populations of ALDH1A1:tdTomato+(CSC) and ALDH1A1:tdTomato-(Non-CSC). 5-DTAF fluorescently labelled non-functionalized micelles (PM:COOH) and the micelles functionalized with the CD300f7 (PM:COOH-F7) and CD300f10 (PM:COOH-F10) peptides were incubated with both cell subpopulations during different time-points. PM uptake was assessed by flow cytometry (Fortessa, BD Biosciences).

Results

Figure 7:
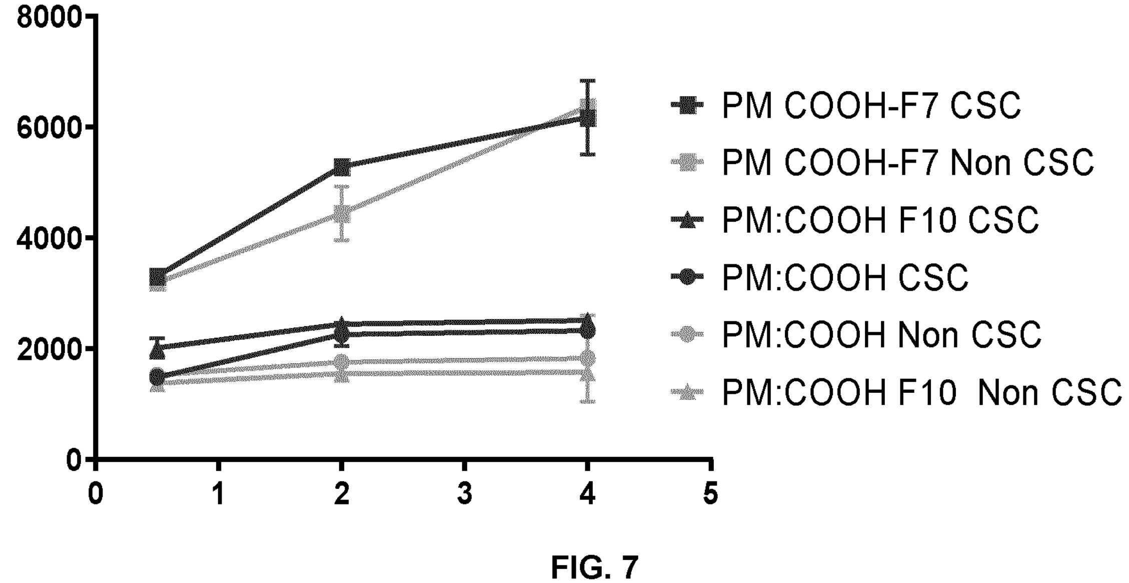
FIG. 7, related to Example 4, shows the internalization profile of various conjugates in MD-MD-231 CSC and non-CSC. FACS quantification of micelles uptake by MDA-MB-231 ALDH1A1/tdTomato positive vs. negative cells. The cells were incubated with the 5-DTAF labeled polymeric micelles (PM) and the intensity of fluorescence was quantified at different time-points (0.5, 2 and 4 hours). Results are expressed as mean±SEM (n=3). The y-axis represents the fluorescence intensity, and the x-axis represents the time in hours.

Internalization of fluorescent-labeled micelles was assessed quantitatively by flow cytometry (FIG. 7). In order to study the uptake profile and to check possible differences in the internalization pattern between CSC and non-CSC, MDA-MB-231-ALDH1A1:tdTomato positive and MDA-MB-231-ALDH1A1:tdTomato negative cells were incubated with 5-DTAF labeled PM:COOH, PM:COOH:F7 and PM:COOH:F10, as described in Example 2.

As previously demonstrated, the PM functionalized with the CD300f7 peptide (SEQ ID NO: 7) (PM:COOH-F7) internalization rate was much higher than for the non-functionalized PM or the PM functionalized with CD300f10 (SEQ ID NO: 18) (PM:COOH:F10). As it is possible to observe, the CD300f7 peptide boost not only the entrance in bulk tumor cells but also in the highly resistant and malignant CSC subpopulation (FIG. 7).

These results demonstrate that the conjugates of the invention are very useful in the treatment of cancer because they can also target CSCs which are thought to be responsible for treatment resistance and cancer relapse.

CITATION LIST

Altschul et al., “Basic local alignment search tool”, 1990, J. Mol. Biol, vol. 215, pp. 403-410.

Copolovici D. M. et al., “Cell-Penetrating Peptides: Design, Synthesis, and Applications”, 2014, ACS Nano, 2014, 8 (3), pp 1972-1994.

Reddy Chichili V P, et al., “Linkers in the structural biology of protein-protein interactions” 2013, Protein Sci., vol. 22:1, pp. 53-167.

Andrade, F., et al., “Biological assessment of self-assembled polymeric micelles for pulmonary administration of insulin”, 2015, Nanomedicine, vol. 11(7), pp. 1621-31.

WO2019129657

WO2014001509

WO2020152298

The invention claimed is:

1. A conjugate comprising:
   - a peptide having a length of 10 to 50 amino acid residues, comprising the amino acid sequence LKXaa$_1$WXaa$_2$Xaa$_3$GAIW (SEQ ID NO: 19), wherein Xaa$_1$, Xaa$_2$, and Xaa$_3$, are each independently any amino acid; and
   - a cargo conjugated to the peptide;
   - wherein the cargo comprises a compound selected from the group consisting of a nucleic acid, a polysaccharide, a lipid, a glycolipid, a polymer, a small molecule, a nanovehicle, and a protein.

2. The conjugate according to claim 1, wherein the nanovehicle is selected from the group consisting of micelle, liposome, extracellular vesicle, nanoemulsion, nanoshell, quantum dot, niosome, dendrimer, inorganic nanoparticle, and combinations thereof.

3. The conjugate according to claim 1, wherein the peptide and the cargo are conjugated via:
   - a covalent bond, optionally mediated by a linker; or alternatively,
   - a non-covalent bond.

4. The conjugate according to claim 1, wherein the protein is selected from the group consisting of an enzyme, an antibody, and a nanobody.

5. The conjugate according to claim 1, wherein at least one of Xaa$_1$ to Xaa$_3$ is selected from the group consisting of:
   - Xaa$_1$ is a non-polar amino acid;
   - Xaa$_2$ is a polar-neutral amino acid; and
   - Xaa$_3$ is a basic amino acid.

6. The conjugate according to claim 1, wherein at least one of Xaa$_1$ to Xaa$_3$ is selected from the group consisting of:
   - Xaa$_1$ is selected from tryptophan and alanine;
   - Xaa$_2$ is selected from cysteine and serine; and
   - Xaa$_3$ is selected from arginine and glycine.

7. The conjugate according to claim 1, wherein the peptide comprises the amino acid sequence LKXaa$_1$WXaa$_2$Xaa$_3$GAIWRDCK (SEQ ID NO: 20), wherein Xaa$_1$, Xaa$_2$, and Xaa$_3$ are each independently any amino acid.

8. The conjugate according to claim 1, wherein the peptide comprises a sequence selected from the group consisting of SEQ ID NO: 4, SEQ ID NO: 5, SEQ ID NO: 6, and SEQ ID NO: 7.

9. The conjugate according to claim 1, wherein the peptide consists of the amino acid sequence selected from the group consisting of LKXaa$_1$WXaa$_2$Xaa$_3$GAIWRDCK (SEQ ID NO: 20), SEQ ID NO: 4, SEQ ID NO: 5, SEQ ID NO: 6, and SEQ ID NO: 7, wherein Xaa$_1$, Xaa$_2$, and Xaa$_3$, are each independently any amino acid.

* * * * *

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid

<400> SEQUENCE: 1

Xaa Lys Xaa Trp Xaa Xaa Xaa Xaa Xaa Trp
1               5                   10


<210> SEQ ID NO 2
<211> LENGTH: 10
<212> TYPE: PRT
<213> ORGANISM: Artificial
<220> FEATURE:
<223> OTHER INFORMATION: peptide

<400> SEQUENCE: 2

Leu Lys Trp Trp Cys Arg Gly Ala Ile Trp
1               5                   10


<210> SEQ ID NO 3
<211> LENGTH: 14
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 3

Xaa Lys Trp Trp Cys Arg Xaa Xaa Xaa Trp Arg Asp Cys Lys
1               5                   10


<210> SEQ ID NO 4
```

```
<211> LENGTH: 14
<212> TYPE: PRT
<213> ORGANISM: Artificial
<220> FEATURE:
<223> OTHER INFORMATION: peptide

<400> SEQUENCE: 4

Leu Lys Trp Trp Cys Arg Gly Ala Ile Trp Arg Asp Cys Lys
1               5                   10


<210> SEQ ID NO 5
<211> LENGTH: 20
<212> TYPE: PRT
<213> ORGANISM: Artificial
<220> FEATURE:
<223> OTHER INFORMATION: peptide

<400> SEQUENCE: 5

Cys Val Tyr Arg Ser Gly Trp Glu Thr Tyr Leu Lys Trp Trp Cys Arg
1               5                   10                  15

Gly Ala Ile Trp
            20


<210> SEQ ID NO 6
<211> LENGTH: 20
<212> TYPE: PRT
<213> ORGANISM: Artificial
<220> FEATURE:
<223> OTHER INFORMATION: peptide

<400> SEQUENCE: 6

Gly Trp Glu Thr Tyr Leu Lys Trp Trp Cys Arg Gly Ala Ile Trp Arg
1               5                   10                  15

Asp Cys Lys Ile
            20


<210> SEQ ID NO 7
<211> LENGTH: 20
<212> TYPE: PRT
<213> ORGANISM: Artificial
<220> FEATURE:
<223> OTHER INFORMATION: peptide

<400> SEQUENCE: 7

Leu Lys Trp Trp Cys Arg Gly Ala Ile Trp Arg Asp Cys Lys Ile Leu
1               5                   10                  15

Val Lys Thr Ser
            20


<210> SEQ ID NO 8
<211> LENGTH: 20
<212> TYPE: PRT
<213> ORGANISM: Artificial
<220> FEATURE:
<223> OTHER INFORMATION: peptide

<400> SEQUENCE: 8

Leu Lys Trp Trp Ser Arg Gly Ala Ile Trp Arg Asp Cys Lys Ile Leu
1               5                   10                  15

Val Lys Thr Ser
            20


<210> SEQ ID NO 9
<211> LENGTH: 20
<212> TYPE: PRT
```

```
<213> ORGANISM: Artificial
<220> FEATURE:
<223> OTHER INFORMATION: peptide

<400> SEQUENCE: 9

Leu Lys Ala Trp Cys Arg Gly Ala Ile Trp Arg Asp Cys Lys Ile Leu
1               5                   10                  15

Val Lys Thr Ser
            20


<210> SEQ ID NO 10
<211> LENGTH: 20
<212> TYPE: PRT
<213> ORGANISM: Artificial
<220> FEATURE:
<223> OTHER INFORMATION: peptide

<400> SEQUENCE: 10

Leu Lys Trp Trp Cys Gly Gly Ala Ile Trp Arg Asp Cys Lys Ile Leu
1               5                   10                  15

Val Lys Thr Ser
            20


<210> SEQ ID NO 11
<211> LENGTH: 12
<212> TYPE: PRT
<213> ORGANISM: Artificial
<220> FEATURE:
<223> OTHER INFORMATION: peptide

<400> SEQUENCE: 11

Gly Arg Lys Lys Arg Arg Gln Arg Arg Arg Pro Gln
1               5                   10


<210> SEQ ID NO 12
<211> LENGTH: 20
<212> TYPE: PRT
<213> ORGANISM: Artificial
<220> FEATURE:
<223> OTHER INFORMATION: peptide

<400> SEQUENCE: 12

Thr Gln Ile Thr Gly Pro Thr Thr Val Asn Gly Leu Glu Arg Gly Ser
1               5                   10                  15

Leu Thr Val Gln
            20


<210> SEQ ID NO 13
<211> LENGTH: 20
<212> TYPE: PRT
<213> ORGANISM: Artificial
<220> FEATURE:
<223> OTHER INFORMATION: peptide

<400> SEQUENCE: 13

Pro Thr Thr Val Asn Gly Leu Glu Arg Gly Ser Leu Thr Val Gln Cys
1               5                   10                  15

Val Tyr Arg Ser
            20


<210> SEQ ID NO 14
<211> LENGTH: 20
<212> TYPE: PRT
<213> ORGANISM: Artificial
<220> FEATURE:
```

<223> OTHER INFORMATION: peptide

<400> SEQUENCE: 14

Gly Leu Glu Arg Gly Ser Leu Thr Val Gln Cys Val Tyr Arg Ser Gly
1 5 10 15

Trp Glu Thr Tyr
20

<210> SEQ ID NO 15
<211> LENGTH: 20
<212> TYPE: PRT
<213> ORGANISM: Artificial
<220> FEATURE:
<223> OTHER INFORMATION: peptide

<400> SEQUENCE: 15

Ser Leu Thr Val Gln Cys Val Tyr Arg Ser Gly Trp Glu Thr Tyr Leu
1 5 10 15

Lys Trp Trp Cys
20

<210> SEQ ID NO 16
<211> LENGTH: 20
<212> TYPE: PRT
<213> ORGANISM: Artificial
<220> FEATURE:
<223> OTHER INFORMATION: peptide

<400> SEQUENCE: 16

Arg Gly Ala Ile Trp Arg Asp Cys Lys Ile Leu Val Lys Thr Ser Gly
1 5 10 15

Ser Glu Gln Glu
20

<210> SEQ ID NO 17
<211> LENGTH: 20
<212> TYPE: PRT
<213> ORGANISM: Artificial
<220> FEATURE:
<223> OTHER INFORMATION: peptide

<400> SEQUENCE: 17

Arg Asp Cys Lys Ile Leu Val Lys Thr Ser Gly Ser Glu Gln Glu Val
1 5 10 15

Lys Arg Asp Arg
20

<210> SEQ ID NO 18
<211> LENGTH: 20
<212> TYPE: PRT
<213> ORGANISM: Artificial
<220> FEATURE:
<223> OTHER INFORMATION: peptide

<400> SEQUENCE: 18

Leu Val Lys Thr Ser Gly Ser Glu Gln Glu Val Lys Arg Asp Arg Val
1 5 10 15

Ser Ile Lys Asp
20

<210> SEQ ID NO 19
<211> LENGTH: 10
<212> TYPE: PRT
<213> ORGANISM: Artificial

-continued

```
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa can be any naturally occurring amino acid

<400> SEQUENCE: 19

Leu Lys Xaa Trp Xaa Xaa Gly Ala Ile Trp
1               5                   10


<210> SEQ ID NO 20
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa can be any naturally occurring amino acid

<400> SEQUENCE: 20

Leu Lys Xaa Trp Xaa Xaa Gly Ala Ile Trp Arg Asp Cys Lys
1               5                   10
```